United States Patent
Adachi et al.

(10) Patent No.: US 7,285,615 B2
(45) Date of Patent: Oct. 23, 2007

(54) PARTICULATE WATER-ABSORBENT RESIN COMPOSITION

(75) Inventors: Yoshifumi Adachi, Himeji (JP); Toshimasa Kitayama, Himeji (JP); Yorimichi Dairoku, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 348 days.

(21) Appl. No.: 10/926,992

(22) Filed: Aug. 27, 2004

(65) Prior Publication Data

US 2005/0049379 A1    Mar. 3, 2005

(30) Foreign Application Priority Data

Sep. 2, 2003   (JP)   ............... 2003-310387

(51) Int. Cl.
   *C08F 2/00*       (2006.01)
   *C08F 120/02*   (2006.01)
   *C08F 20/06*     (2006.01)
   *A61F 13/00*     (2006.01)

(52) U.S. Cl. ................. 526/319; 526/329.7; 526/317.1; 428/402

(58) Field of Classification Search ............. 526/317.1, 526/319, 329.7; 525/301; 428/402
   See application file for complete search history.

(56) References Cited

U.S. PATENT DOCUMENTS

| | | | |
|---|---|---|---|
| 4,093,776 A | 6/1978 | Aoki et al. | |
| 4,367,323 A | 1/1983 | Kitamura et al. | |
| 4,446,261 A | 5/1984 | Yamasaki et al. | |
| 4,625,001 A | 11/1986 | Tsubakimoto et al. | |
| 4,683,274 A | 7/1987 | Nakamura et al. | |
| 4,690,996 A | 9/1987 | Shih et al. | |
| 4,721,647 A | 1/1988 | Nakanishi et al. | |
| 4,734,478 A | 3/1988 | Tsubakimoto et al. | |
| RE32,649 E | 4/1988 | Brandt et al. | |
| 4,738,867 A | 4/1988 | Itoh et al. | |
| 4,748,076 A | 5/1988 | Saotome | |
| 4,769,427 A | 9/1988 | Nowakowsky et al. | |
| 4,873,299 A | 10/1989 | Nowakowsky et al. | |
| 4,950,692 A | 8/1990 | Lewis et al. | |
| 5,061,259 A | 10/1991 | Goldman et al. | |
| 5,064,582 A | 11/1991 | Sutton et al. | |
| 5,264,495 A | 11/1993 | Irie et al. | |
| 5,397,845 A * | 3/1995 | Rebre et al. ................. | 525/301 |
| 5,478,879 A | 12/1995 | Kajikawa et al. | |
| 5,601,542 A | 2/1997 | Melius et al. | |
| 5,714,156 A | 2/1998 | Schmidt et al. | |
| 5,817,865 A | 10/1998 | Machhammer et al. | |
| 5,849,405 A | 12/1998 | Wang et al. | |
| 6,068,924 A | 5/2000 | Palumbo | |
| 6,121,509 A | 9/2000 | Ashraf et al. | |
| 6,159,591 A | 12/2000 | Beihoffer et al. | |
| 6,333,109 B1 | 12/2001 | Harada et al. | |
| 6,342,652 B1 | 1/2002 | Harada et al. | |
| 6,534,554 B1 | 3/2003 | Mitchell et al. | |
| 6,586,549 B1 | 7/2003 | Hatsuda et al. | |
| 6,596,901 B1 | 7/2003 | Eck et al. | |
| 2001/0001312 A1 | 5/2001 | Mitchell et al. | |
| 2001/0006267 A1 | 7/2001 | Harada et al. | |
| 2001/0016668 A1 | 8/2001 | Mitsumoto et al. | |
| 2002/0035353 A1 | 3/2002 | Chmielewski et al. | |
| 2002/0091366 A1 | 7/2002 | Abrahamsson | |
| 2003/0020199 A1 * | 1/2003 | Kajikawa et al. ........... | 264/140 |
| 2003/0060112 A1 | 3/2003 | Rezai et al. | |
| 2003/0138631 A1 | 7/2003 | Mitchell et al. | |
| 2003/0144379 A1 | 7/2003 | Mitchell et al. | |
| 2004/0180189 A1 | 9/2004 | Funk et al. | |

FOREIGN PATENT DOCUMENTS

| | | |
|---|---|---|
| EP | 0 812 873 | 12/1997 |
| EP | 0 844 270 | 5/1998 |
| EP | 0 885 917 | 12/1998 |
| EP | 1 178 059 | 2/2002 |
| EP | 1 426 402 | 6/2004 |
| JP | 6-57010 | 3/1994 |
| JP | 6-313043 | 11/1994 |
| WO | WO 95/22356 | 8/1995 |
| WO | WO 96/15180 | 5/1996 |
| WO | WO 98/24832 | 6/1998 |
| WO | WO 98/37149 | 8/1998 |
| WO | WO 99/25393 | 5/1999 |
| WO | WO 99/30751 | 6/1999 |
| WO | WO 99/34841 | 7/1999 |
| WO | WO 99/34843 | 7/1999 |
| WO | WO 00/55258 | 9/2000 |
| WO | WO 01/47568 | 7/2001 |
| WO | WO 01/47569 | 7/2001 |
| WO | WO 01/47570 | 7/2001 |
| WO | WO 03/028778 | 4/2003 |
| WO | WO 03/043671 | 5/2003 |
| WO | WO 2004/069293 | 8/2004 |

* cited by examiner

*Primary Examiner*—David W. Wu
*Assistant Examiner*—M. Bernshteyn
(74) *Attorney, Agent, or Firm*—Roylance, Abrams, Berdo & Goodman, L.L.P.

(57) ABSTRACT

An object of the present invention is to provide a particulate water-absorbent resin composition which is so excellent that: the absorption ability in an initial short time is secured in some degree, and further, the absorption capacity lastingly increases over a long period, and also the liquid permeability and the liquid diffusibility can be secured. As a means of achieving this object, a particulate water-absorbent resin composition according to the present invention is a particulate water-absorbent resin composition comprising a carboxyl-group-containing water-absorbent resin in an amount of not smaller than 80 mass %, with the composition being characterized by being: not less than 20 g/g in specific-particle-diameter absorption capacity under load (0.29 psi (2.00 kPa), 1 hour); and not less than 3 g/g in specific-particle-diameter absorption index increment in 20 hours.

19 Claims, 1 Drawing Sheet

PARTICULATE WATER-ABSORBENT RESIN COMPOSITION

BACKGROUND OF THE INVENTION

A. Technical Field

The present invention relates to a particulate water-absorbent resin composition. More specifically, the present invention relates to a particulate water-absorbent resin composition which is so excellent as to be able to exhibit a high absorption capacity over a long period when used for sanitary materials such as disposable diapers, sanitary napkins, and incontinent pads.

B. Background Art

At present, water-absorbent resins, their compositions, and hydrophilic fibers (e.g. pulp) are widely used for sanitary materials such as disposable diapers, sanitary napkins, and so-called incontinent pads as their component materials for the purpose of absorption of body fluids. Examples of materials used as main raw materials for the above water-absorbent resins include: partially-neutralized and crosslinked poly(acrylic acids); hydrolyzed graft polymers of starch-acrylic acid; saponified copolymers of vinyl acetate-acrylic acid esters; hydrolyzed copolymers of acrylonitrile or acrylamide, or crosslinked polymers of these hydrolyzed copolymers; and crosslinked polymers of cationic monomers.

In recent years, as to the sanitary materials such as disposable diapers and sanitary napkins, their high functionalization and thinning are making progress, so there is a tendency toward increases in the amount of the water-absorbent resin as used per piece of sanitary material and in the mass ratio of the water-absorbent resin relative to a whole absorbent structure consisting of such as the water-absorbent resin and the hydrophilic fibers. Specifically, the content of the water-absorbent resin in the absorbent structure is raised by decreasing the amount of the hydrophilic fibers (which have a small bulk density) and increasing the amount of the water-absorbent resin (which has excellent water absorbency and a large bulk density) as used. Thereby the thinning of the sanitary materials is aimed at without lowering the water absorption quantity.

When the performances of the water-absorbent resin are evaluated, commonly, the evaluations have hitherto been carried out by such as absorption capacity without load, absorption capacity under load, and absorption index under load (e.g. refer to patent document 1 below).

In conventional methods for evaluation of the water-absorbent resin, generally, it has been common that the absorption capacity in 1 hour from the absorption initiation is measured. Its reason is that conventional water-absorbent resins almost reach no less than their saturated absorption capacities in 1 hour from the absorption initiation.

However, if attention is directed to practical use for diapers, then the diapers are worn for a period of several hours and, in this wearing period, urine is discharged several times at intervals of about tens of minutes to about 1 hour.

Accordingly, as properties of water-absorbent resins suitable for uses such as diapers, it is demanded that: the saturation is not reached in 1 hour, but the absorption ability in an initial short time is secured in some degree, and further, the absorption capacity lastingly increases over a long period, and also the liquid permeability and the liquid diffusibility can be secured. Particularly, in recent years when the thinning makes progress, it is demanded that a high absorption capacity under load can be exhibited over a long period.

Almost all conventional water-absorbent resins almost reach no less than their saturated absorption capacities in 1 hour as mentioned above. Among them, there is a water-absorbent resin which exhibits an extremely low absorption capacity under load. Because such a water-absorbent resin is weak in gel strength and can secure neither the liquid permeability nor the liquid diffusibility, it has had problems when used for such as diapers. It is well known that: when practically used for such as diapers, such a water-absorbent resin swells only in the neighborhood of the urination portion to thus cause gel-blocking, so that it becomes impossible to diffuse urine all over the absorbent structure, thus resulting in inferior absorption performances. This is remarkable particularly as to such a high-concentration absorbent structure as has a water-absorbent resin concentration of higher than 40% or 50% in the absorbent structure.

In addition, it is commonly known that: the lower absorption capacity without load the water-absorbent resin exhibits, the higher its liquid permeability and liquid diffusibility are. However, there has been a problem that, in the case where a water-absorbent resin which exhibits a low absorption capacity is used for practical diapers, its ability to take a liquid into the diapers (liquid permeability) is high, but the absorption quantities of the diapers unfavorably decrease.

A way of making the absorption capacity increase lastingly over a long period is to enlarge the particle diameters of the water-absorbent resin. However, there has been a problem that: if the particle diameters are enlarged, then the use for diapers involves the texture deterioration of diaper surfaces to thus give users a foreign substance feeling.

There are reported some arts in which a mixed-bed type ion-exchange resin is applied in order to make the absorption capacity increase lastingly over a long period.

There is reported a superabsorbent material including a combination of an anionic superabsorbent material in which 20 to 100% of functional groups are free-acid types and an anion exchanger in which 20 to 100% of functional groups are basic types (e.g. refer to patent document 2 below).

There is reported a composition which is a mixed-bed type ion-exchange water-absorbent resin composed of a mixture of a free-functional-group-containing water-swellable anion exchanger and a free-functional-group-containing water-swellable cation exchanger and is characterized in that the absorption capacity under load (0.7 psi (4.83 kPa)) PUP (Performance Under Pressure) is not less than 30 g/g in 2 hours or not less than 40 g/g in 8 hours or not less than 42 g/g in 16 hours (e.g. refer to patent document 3 below).

There is reported a water-absorbent resin in which a microdomain is formed in one particle by a water-absorbent resin in which functional groups exhibiting the basicity exist in a free state and a water-absorbent resin in which functional groups exhibiting the acidity exist in a free state (e.g. refer to patent document 4 below).

All in the above arts, the technology of the mixed-bed type ion-exchange resin is applied to water-absorbent resins, and salts dissolved in urine are taken into functional groups on the water-absorbent resin by ion exchange, whereby the salt concentration of the urine to be absorbed is reduced, and also the osmotic pressure is generated by the dissociation of ions from the functional groups, so that a higher absorption capacity is exhibited. Accordingly, in the above arts, the deceleration of the absorption rate is achieved by adjusting the ion-exchange rate.

However, the above arts have a demerit such that: in the case where the resin is exposed to an aqueous liquid having a salt concentration more than the ion-exchange capacity, the ion exchange occurs, but it does not attain the reduction of such a high salt concentration, so that the swelling capacity sharply deteriorates. In addition, many of the cationic super-absorbent materials (anion exchangers) are extremely expensive, and it has therefore been difficult to provide an inexpensive water-absorbent resin.

In addition, there is also reported an art in which fine particles of poly(acrylic acid) (corresponding to not larger than 45 μm) are added to water-absorbent resin particles to thereby control the liquid permeability (e.g. refer to patent document 5 below). Furthermore, as an art for obtaining a water-absorbing agent by mixing water-absorbent resin particles having different neutralization degrees, such an art is reported also for the purpose of deodorization of such as ammonia (e.g. refer to patent document 6 below). However, this art has a demerit such that: the absorption capacity under load is low, and also, there is almost no effect or only a small effect of increasing the absorption capacity over a long period.

[Patent Document 1] U.S. Pat. No. 5,601,542
[Patent Document 2] Pamphlet of WO 96/15180
[Patent Document 3] Pamphlet of WO 99/34843
[Patent Document 4] Pamphlet of WO 99/25393
[Patent Document 5] JP-A-098170/2001 (Kokai)
[Patent Document 6] Pamphlet of WO 03/28778

SUMMARY OF THE INVENTION

A. Object of the Invention

Accordingly, an object of the present invention is to provide a particulate water-absorbent resin composition which is so excellent as to prevent the occurrence of such as urine leakage over a long period when used for sanitary materials such as disposable diapers and sanitary napkins.

B. Disclosure of the Invention

The present inventors diligently studied to solve the above problems. As a result, the present inventors have considered it important for the solution of the problems that: the absorption ability in an initial short time is secured in some degree, and further, the absorption capacity lastingly increases over a long period, and also the liquid permeability and the liquid diffusibility are secured. Specifically, the present inventors have considered it important that: as properties of the particulate water-absorbent resin composition, there are satisfied the following: a specific-particle-diameter absorption capacity under load in a specific range and a specific-particle-diameter absorption index increment in a specific range; and/or a mass-average particle diameter in a specific range, an absorption capacity under load in a specific range, and an absorption index increment in a specific range. Thus, the present invention has been completed.

In addition, as an example for obtaining the water-absorbent resin composition according to the present invention which satisfies novel parameters, the present inventors first took notice of relations between the neutralization degree and absorption capacity of a carboxyl-group-containing water-absorbent resin. Specifically, the present inventors took notice that there is seen a peculiar phenomenon such that: although the absorption capacity of the carboxyl-group-containing water-absorbent resin increases with the increase of the neutralization degree, the extent of this increase of the absorption capacity is not constant, but a sharp increase of the absorption capacity is seen until the neutralization degree reaches about 50%, and then the increase of the absorption capacity becomes gentle if the neutralization degree increases to not less than about 50%.

Next, the present inventors considered using a mixture of a carboxyl-group-containing water-absorbent resin having a lower neutralization degree of which the extent of the increase of the absorption capacity is larger and a carboxyl-group-containing water-absorbent resin having a higher neutralization degree of which the extent of the increase of the absorption capacity is smaller. As a result, it has been found that: if at least two kinds of carboxyl-group-containing water-absorbent resins having different neutralization degrees are mixed together in this way, then, surprisingly, the absorption ability in an initial short time is secured in some degree, and further, the absorption capacity lastingly increases over a long period, and also the liquid permeability and the liquid diffusibility can be secured, when compared with the case where only one kind of carboxyl-group-containing water-absorbent resin having a definite neutralization degree is used.

Furthermore, it has also been found to be favorable for exhibiting such a function that the particle diameters are regulated in a certain specific range.

That is to say, a first particulate water-absorbent resin composition according to the present invention is a particulate water-absorbent resin composition comprising a carboxyl-group-containing water-absorbent resin in an amount of not smaller than 80 mass %, with the composition being characterized by being: not less than 20 g/g in specific-particle-diameter absorption capacity under load (0.29 psi (2.00 kPa), 1 hour); and not less than 3 g/g in specific-particle-diameter absorption index increment in 20 hours.

In addition, a second particulate water-absorbent resin composition according to the present invention is a particulate water-absorbent resin composition comprising a carboxyl-group-containing water-absorbent resin in an amount of not smaller than 80 mass %, with the composition being characterized by being: in the range of 320 to 700 μm in mass-average particle diameter; not less than 20 g/g in absorption capacity under load (0.3 psi (2.06 kPa), 1 hour); and not less than 3 g/g in absorption index increment in 20 hours.

Furthermore, a water-absorbent article according to the present invention comprises a particulate water-absorbent resin composition according to the present invention.

C. Effects of the Invention

The present invention can provide a particulate water-absorbent resin composition which is so excellent that: the absorption ability in an initial short time is secured in some degree, and further, the absorption capacity lastingly increases over a long period, and also the liquid permeability and the liquid diffusibility can be secured. Besides, if such a particulate water-absorbent resin composition is used for water-absorbent articles such as disposable diapers, then the absorption performances of the water-absorbent articles can be enhanced, so that problems of such as leakage can be avoided.

These and other objects and the advantages of the present invention will be more fully apparent from the following detailed disclosure.

DETAILED DESCRIPTION OF THE INVENTION

Figure 1:
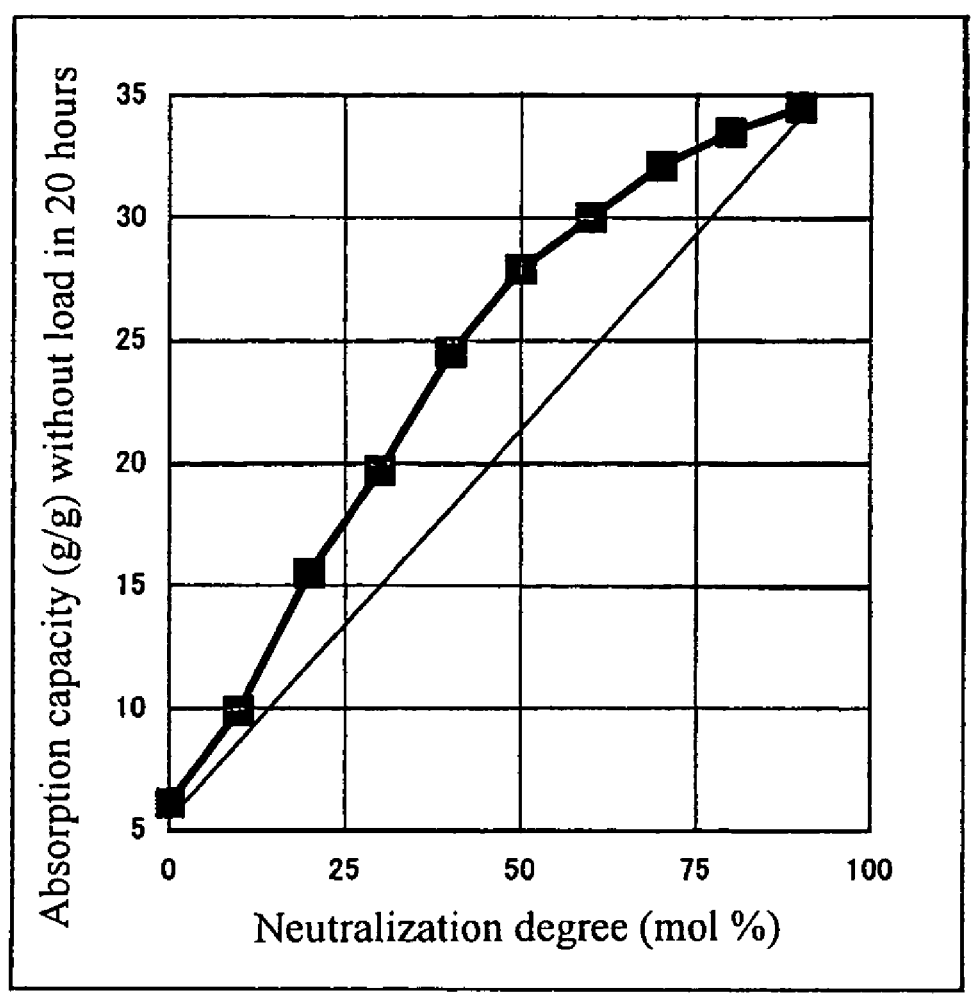
FIG. 1 is a graph of relations between neutralization degree and absorption capacity, illustrating the results of Referential Example 1.

Hereinafter, detailed descriptions are given about the present invention. However, the scope of the present invention is not bound to these descriptions. And other than the following illustrations can also be carried out in the form of appropriate modifications of the following illustrations within the scope not departing from the spirit of the present invention.

[Water-absorbent Resin]:

In the present invention, the water-absorbent resin, for example, refers to a hitherto publicly known crosslinked polymer which absorbs water in a large amount of essentially not smaller than 5 times, favorably in the range of 50 to 1,000 times, of the own weight in deionized water to thus form an anionic, nonionic, or cationic water-insoluble hydrogel.

Incidentally, as to the particulate water-absorbent resin composition as referred to in the present invention, if it comprises the water-absorbent resin as a main component (comprises a carboxyl-group-containing water-absorbent resin as an essential component in an amount of 80 to 100 mass % of the solid components of the composition), then the content of components other than the water-absorbent resin may be 0 mass %. In addition, not only in the case where the water-absorbent resin used as the main component of the composition is a mixture of at least two different water-absorbent resins (e.g. water-absorbent resins different from each other in such as polymer composition, production process, water absorption capacity, or particle diameter distribution), but also in the case where the water-absorbent resin used as the main component of the composition is a single water-absorbent resin alone, such a composition is referred to as particulate water-absorbent resin composition in the present invention. That is to say, the particulate water-absorbent resin composition as referred to in the present invention is a synonym of a particulate water-absorbing agent comprising the water-absorbent resin as a main component, and can be reworded into the particulate water-absorbing agent comprising the water-absorbent resin as a main component. Incidentally, it is the same as the descriptions of U.S. Pat. Nos. 5,061,259 and Re. 32,649 that the single water-absorbent resin alone is also referred to as water-absorbent resin composition.

The water-absorbent resin, used in the present invention, needs to be water-swellable and water-insoluble. The uncrosslinked water-extractable component (water-soluble polymer) content of the water-absorbent resin as used is favorably not higher than 50 mass %, more favorably not higher than 25 mass %, still more favorably not higher than 20 mass %, yet still more favorably not higher than 15 mass %, particularly favorably not higher than 10 mass %.

Examples of the water-absorbent resin include: partially-neutralized polymers of poly(acrylic acids); hydrolyzed graft polymers of starch-acrylonitrile; graft polymers of starch-acrylic acid; saponified copolymers of vinyl acetate-acrylic acid esters; hydrolyzed copolymers of acrylonitrile or acrylamide, or crosslinked polymers of these hydrolyzed copolymers; modified polymers of carboxyl-group-containing crosslinked polyvinyl alcohols; and crosslinked copolymers of isobutylene-maleic anhydride.

The water-absorbent resins may be used either alone respectively or in combinations with each other.

In the present invention, it is favorable to use a carboxyl-group-containing water-absorbent resin.

The carboxyl-group-containing water-absorbent resin, as referred to in the present invention, is a three-dimensionally crosslinked polymer of a hydrophilic polymer having carboxyl groups (which are shown by —COOM as a general formula (M=such as hydrogen, alkaline metal, alkaline earth metal, amine, or ammonium)) as side chains. Hereupon, in the case of M=H, the carboxyl-group-containing water-absorbent resin may be called "unneutralized water-absorbent resin" or "acid type". In the case of other than M=H, the carboxyl-group-containing water-absorbent resin may be called "neutralized water-absorbent resin" or "salt".

Specific examples of the carboxyl-group-containing water-absorbent resin include: a water-absorbent resin including as a main component a crosslinked polymer which is obtained by a process including the step of crosslink-polymerizing a monomer component including a carboxyl-group-containing monomer (e.g. (meth)acrylic acid, (anhydrous) maleic acid, fumaric acid, crotonic acid, itaconic acid, cinnamic acid) and/or its salt as a main component; and further a water-absorbent resin which is obtained by a process including the step of crosslinking a carboxyl-group-containing polymer (e.g. poly((meth)acrylic acid), carboxymethyl cellulose) and/or its salt. Particularly above all, there is preferred the water-absorbent resin including as a main component the crosslinked polymer which is obtained by the process including the step of crosslink-polymerizing the monomer component including acrylic acid and/or its salt as a main component. The aforementioned crosslinked polymer may contain a grafted component if necessary.

As examples of the acrylic acid salt, there can be cited such as: alkaline metal (e.g. sodium, potassium, lithium) salts, ammonium salts, and amine salts of acrylic acid.

Incidentally, as to the acrylic acid salt as used, hitherto publicly known ones are usable. For example, they are disclosed in such as USP (application publication) 2001/0016668, U.S. Pat. Nos. 5,817,865, and 6,596,901.

In the carboxyl-group-containing water-absorbent resin used in the present invention, the neutralization degree indicates a molar ratio between the entire carboxyl groups contained in the carboxyl-group-containing water-absorbent resin and salts of carboxyl groups (those which have counter-cations other than M=hydrogen) contained in this resin and is a parameter indicating the ratio of what are neutralized. The neutralization of the water-absorbent resin for forming the above salt may be carried out in a monomer state before the polymerization, or may be carried out in a polymer state on the way of or after the polymerization, or may be carried out both in these states.

As monomers to obtain the water-absorbent resin as used in the present invention, there may be included monomers other than the above carboxyl-group-containing monomers and/or their salts.

There is no especial limitation on the monomers other than the carboxyl-group-containing monomers and/or their salts. However, specific examples thereof include: anionic unsaturated monomers (e.g. vinylsulfonic acid, styrenesulfonic acid, 2-(meth)acrylamido-2-methylpropanesulfonic acid, 2-(meth)acryloylethanesulfonic acid, 2-(meth)acryloylpropanesulfonic acid) and their salts; nonionic-hydrophilic-group-containing unsaturated monomers (e.g. acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono (meth)acrylate, vinylpyridine, N-vinylpyrrolidone, N-acryloylpiperidine, N-acryloylpyrrolidine, N-vinylacetamide); and cationic unsaturated monomers (e.g. N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide, and their quaternary salts). These monomers may be used either alone respectively or in appropriate combinations with each other.

In the present invention, when the monomers other than the carboxyl-group-containing monomers and/or their salts are used, the ratio in which these monomers other than the carboxyl-group-containing monomers and/or their salts are used is favorably not more than 30 mol %, more favorably not more than 10 mol %, relative to the total of the carboxyl-group-containing monomers and/or their salts used as the main components. If the monomers other than the carboxyl-group-containing monomers and/or their salts are used in the above ratio, then the absorption properties of the water-absorbent resin and particulate water-absorbent resin composition being finally obtained are still more enhanced, and further, the water-absorbent resin and particulate water-absorbent resin composition can be obtained at still lower costs.

When the above monomer is polymerized in order to obtain the water-absorbent resin as used in the present invention, it is possible to carry out bulk polymerization or precipitation polymerization. However, from the viewpoints of the performance, the facility of polymerization control, and the absorption properties of a swollen gel, it is favorable to carry out aqueous solution polymerization or reversed-phase suspension polymerization in which the above monomer is used in the form of an aqueous solution.

Polymerization methods for the aqueous solution polymerization and reversed-phase suspension polymerization have hitherto been known in public and are disclosed in such as U.S. Pat. Nos. 4,625,001, 4,769,427, 4,873,299, 4,093,776, 4,367,323, 4,446,261, 4,683,274, 4,690,996, 4,721,647, 4,738,867, 4,748,076, and EP 1178059.

In the case where the monomer is used in the form of an aqueous solution, the concentration of the monomer in this aqueous solution (hereinafter referred to as aqueous monomer solution) depends on the temperature of the aqueous monomer solution or the kind of the monomer and is therefore not especially limited. However, this concentration is favorably in the range of 10 to 70 mass %, more favorably 20 to 60 mass %. In addition, when the above aqueous solution polymerization is carried out, a solvent other than water may be used jointly therewith if necessary. The kind of this solvent which is jointly used is not especially limited.

Examples of the method for the aqueous solution polymerization include: a method in which the aqueous monomer solution is polymerized while the resulting hydrogel is crushed in a twin-arm type kneader; and a method in which the aqueous monomer solution is supplied into a predetermined container or onto a moving belt to carry out the polymerization and then the resultant gel is pulverized with such as a meat chopper.

When the polymerization is initiated, there can be used, for example, the following: radical polymerization initiators such as potassium persulfate, ammonium persulfate, sodium persulfate, t-butyl hydroperoxide, hydrogen peroxide, and 2,2'-azobis(2-amidinopropane) dihydrochloride; and photo-initiators such as 2-hydroxy-2-methyl-1-phenyl-propan-1-one.

Furthermore, a redox initiator is also available by using the above polymerization initiator jointly with a reducing agent which promotes the decomposition of the above polymerization initiator and thus combining both with each other.

Examples of the reducing agent include: (bi)sulfurous acid (salts) such as sodium sulfite and sodium hydrogensulfite; L-ascorbic acid (salts); reducible metals (salts) such as ferrous salts; and amines. However, there is no especial limitation thereto.

The amount of the polymerization initiator as used is favorably in the range of 0.001 to 2 mol %, more favorably 0.01 to 0.1 mol %. In the case where the amount of the polymerization initiator as used is smaller than 0.001 mol %, there are disadvantages in that: the amount of unreacted monomers increases, and therefore the amount of residual monomers increases in the resultant water-absorbent resin and particulate water-absorbent resin composition. In the case where the amount of the polymerization initiator as used is larger than 2 mol %, there are disadvantages in that the water-extractable component content in the resultant water-absorbent resin and particulate water-absorbent resin composition increases.

The initiation of the polymerization reaction may be carried out by irradiating the reaction system with active energy rays such as radiations, electron beams, and ultra-violet rays. Furthermore, the above polymerization initiator may be used jointly therewith.

The reaction temperature in the polymerization reaction is not especially limited. However, the reaction temperature is favorably in the range of 10 to 130° C., more favorably 15 to 120° C., particularly favorably 20 to 100° C.

The reaction duration or polymerization pressure in the polymerization reaction is also not especially limited, but may be set appropriately for such as the kind of the monomer or polymerization initiator and the reaction temperature.

The water-absorbent resin may be a self-crosslinked-type water-absorbent resin obtained without any crosslinking agent, but it is preferably a water-absorbent resin obtained by copolymerization or reaction with a crosslinking agent having at least two polymerizable unsaturated groups and/or at least two reactive groups per molecule (internal-crosslinking agent for water-absorbent resins) or with a crosslinking agent which is a cyclic compound and will have at least two reactive groups per molecule by its ring-opening reaction.

Specific examples of the internal-crosslinking agents include: N,N'-methylenebis(meth)acrylamide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether; polyhydric alcohols such as ethylene glycol, polyethylene glycol, propylene glycol, 1,3-butanediol, 1,4-butanediol, glycerol, and pentaerythritol; and ethylenediamine, ethylene carbonate, propylene carbonate, polyethylenimine, and glycidyl (meth)acrylate.

The internal-crosslinking agents may be used either alone respectively or in appropriate combinations with each other.

The internal-crosslinking agents may be added to the reaction system either in a lump or divisionally.

In the case where the internal-crosslinking agent is used, it is favorable, in consideration of such as absorption properties of the finally obtained water-absorbent resin and particulate water-absorbent resin composition, that a compound having at least two polymerizable unsaturated groups is essentially used during the polymerization.

The amount of the internal-crosslinking agent as used is favorably in the range of 0.001 to 2 mol %, more favorably 0.02 to 1.0 mol %, still more favorably 0.06 to 0.30 mol %, particularly favorably 0.08 to 0.15 mol %, relative to the aforementioned monomer (exclusive of the internal-crosslinking agents). In the case where the amount of the internal-crosslinking agent as used is smaller than 0.001 mol % or larger than 2 mol %, there is a possibility that no sufficient absorption properties can be obtained.

In the case where the internal-crosslinking agent is used to introduce a crosslinked structure into the inside of the polymer, it is enough that the internal-crosslinking agent is added to the reaction system before, on the way of, or after the polymerization of the monomer, or after the neutralization. However, it is favorable to carry out the addition before the polymerization.

When the polymerization is carried out, to the reaction system there can be added such as: hydrophilic polymers (e.g. starch, cellulose, starch derivatives, cellulose derivatives, polyvinyl alcohol, poly(acrylic acid) (salts), and crosslinked poly(acrylic acid) (salts)) in the range of 0 to 50 mass % (relative to the monomer); and further, other materials (e.g. various foaming agents such as (hydrogen)carbonates, carbon dioxide, azo compounds, and inert organic solvents; various surfactants; chelating agents; chain transfer agents such as hypophosphorous acid (salts); inorganic fine particles such as kaolin, talc, and silicon dioxide; polyvalent metal salts such as poly(aluminum chloride), aluminum sulfate, and magnesium sulfate) in the range of 0 to 10 mass % (relative to the monomer).

When the crosslinked polymer (having been formed by introducing the crosslinked structure into the inside of the polymer with the internal-crosslinking agent) is obtained by the aqueous solution polymerization and is a gel, namely, a crosslinked hydrogel polymer, then this crosslinked hydrogel polymer is divided into small pieces, if necessary, and then dried and pulverized. The pulverization may be carried out at any time of before, at the same time as, and after the drying. Favorably, the pulverization is carried out after the drying.

In the present invention, favorably, the drying is carried out to a hydrogel polymer which is particulate (its mass-average particle diameter is, for example, not larger than 2 cm, favorably not larger than 1 cm, more favorably not larger than 5 mm). As to the method of the division into small pieces for forming the hydrogel polymer into the particulate one in the present invention, the division into small pieces may be carried out either at the same time as the polymerization with such as a kneader or separately after the polymerization, or the division into small pieces during the polymerization may be used jointly with the division into small pieces after the polymerization. Incidentally, in the case where the hydrogel polymer is not dried in the particulate state, for example, is dried in a filmy state, there is a possibility that the resultant physical properties or particle diameters may be inferior.

As to the particle diameters of the crosslinked hydrogel polymer before drying, the mass-average particle diameter is favorably in the range of 45 to 4,000 µm, more favorably 50 to 2,000 µm, still more favorably 100 to 1,500 µm, particularly favorably 200 to 1,000 µm, in consideration of the drying efficiency and the physical properties.

Examples of apparatuses suitable for the division into small pieces include a kneader, a vertically cutting type slitter having cutter blades, a horizontally cutting type slitter having cutter blades, a cutter type pulverizer having rotary blades, and a meat chopper having a predetermined aperture diameter. Incidentally, in the case where the mass-average particle diameter of the hydrogel polymer deviates from the above range, there is a possibility such that the water absorption capacity of the resultant water-absorbent resin may be low, or that its water-extractable component content may be high.

The hydrogel polymer, as obtained in the above way, favorably gets dried. The drying refers to putting the hydrogel polymer in a solid state with a solid component content of favorably not less than 80 mass %, more favorably not less than 85 mass %, still more favorably not less than 90 mass %, particularly favorably not less than 93 mass %. Incidentally, the drying, as hereupon referred to, does not need to give a dry polymer having a solid component content of 100 mass % (water content: 0).

The drying method, usable in the present invention, is not especially limited. Examples thereof include drying methods such as hot-air drying, thin-film drying (with such as a drum dryer), reduced pressure drying, stir-drying, and fluidized-bed drying. These drying methods may be used either alone respectively or in combinations with each other, and it doesn't especially matter whether the drying type is a continuous type or batch type. In the present invention, the hot-air drying, particularly, continuous hot-air drying, is preferably used in consideration of the physical properties and the drying efficiency and, for example, the continuous hot-air drying may be carried out by static drying on a belt.

From the viewpoint of the drying efficiency, the hot-air drying may, for example, be carried out by layering the particulate hydrogel polymer on a metal gauze and/or a punching metal with apertures or slits and then passing a hot airflow through spaces between the layered particles in a vertical or horizontal direction, preferably in a vertical direction, of the gel. As to the aperture diameter of the metal gauze as used, for a example, the aperture or metal gauze may have aeration holes of the diameter of favorably about 0.1 to about 5 mm, more favorably about 0.2 to about 2 mm. As to the layering of the gel on the metal gauze or the punching metal, the particulate hydrogel polymer may be layered into a definite thickness of favorably 1 to 20 cm, more favorably 1.5 to 10 cm, still more favorably 2 to 8 cm, in consideration of the physical properties resultant from the drying step.

When drying the hydrogel polymer, the drying temperature is, usually, favorably not lower than 100° C., more favorably in the range of 110 to 230° C., still more favorably 130 to 200° C., particularly favorably 150 to 190° C., in consideration of the physical properties and the productivity. The drying temperature is determined by the material temperature or the temperature of the heat medium (e.g. hot air), but, preferably, is determined by the temperature of the heat medium. The drying temperature may be constant through the drying period, or may be changed fitly in the above temperature range on a way of the drying. When the hot-air drying is carried out, the dew point of the hot air is favorably in the range of 40 to 100° C., more favorably 50 to 90° C., still more favorably 60 to 85° C., from the viewpoint of the physical properties and the energy efficiency.

The particulate hydrogel polymer having been dried in the layered state tends to be a blocky dried material having lost the flowability due to aggregation between particles as a result of the drying. Such a blocky dried material is an aggregate of particles of the dried polymer and therefore has continuous spaces and gas permeability through the blocks, but has non-flowability due to the aggregation. Therefore, there is a case where the pulverization (disintegration) step is needed.

The pulverization may be carried out at any time of before, at the same time as, and after the drying, but favorably the pulverization is carried out after the drying.

More favorably, further the classification is carried out after the pulverization. The drying and the pulverization, and further, if necessary, the classification, are favorably carried out in a series of steps.

The pulverization method is free of especial limitation if the dried polymer or its aggregate (blocky material) can be formed into a flowable powder, preferably a powder having a mass-average particle diameter of not larger than 2 mm. Examples thereof include: a pulverization method involving the use of a hammer type pulverizer, a roll type pulverizer, or a jet air stream type pulverizer; and hitherto publicly known various pulverization or disintegration methods. These methods may be used either alone respectively or in combinations with each other. In addition, in the case where the aggregation is weak in the drying step, the pulverization may be carried out by classifying the dried polymer while vibrating it, thereby loosening the aggregation of the polymer, even if no pulverizer is especially used.

After the pulverization, coarse particles and/or fine powders may be removed by favorably further carrying out the classification, if necessary.

When the water-absorbent resin used in the present invention is obtained, the classification may be carried out for control to a specific particle diameter distribution.

Although not especially limited, examples of classifiers as used in the case of carrying out the classification include shaking sieves (e.g. unbalanced-weight driving types, resonance types, shaking motor types, electromagnetic types, circular shaking types), in-plane motion sieves (e.g. horizontal motion types, horizontal circle-straight line motion types, three-dimensional circular motion types), movable-mesh type sieves, forced-stirring type sieves, mesh-face-shaking type sieves, wind power sieves, and sound wave sieves. Favorably, the shaking sieves and the in-plane motion sieves are used.

Water-absorbent resin particles as obtained in this way are favorably adjusted to specific particle diameters. As to these particle diameters, the content of particles having particle diameters of smaller than 850 μm but not smaller than 150 μm is favorably not lower than 90 mass %, more favorably not lower than 95 mass %, still more favorably not lower than 97 mass %.

The mass-average particle diameter of the water-absorbent resin particles as obtained in this way is determined according to purposes. However, favorably for sufficiently exercising the effects of the present invention, the mass-average particle diameter (D50) is in the range of 300 to 700 μm, more favorably 320 to 700 μm, still more favorably 330 to 700 μm, yet still more favorably 340 to 700 μm, yet still more favorably 360 to 700 μm, yet still more favorably 380 to 700 μm, particularly favorably 400 to 700 μm.

In addition, the content of the water-absorbent resin particles having particle diameters of smaller than 150 μm is favorably in the range of 0 to 10 mass % (but not including 10 mass %), more favorably 0 to 7 mass % (but not including 7 mass %), still more favorably 0 to 5 mass % (but not including 5 mass %), particularly favorably 0 to 3 mass % (but not including 3 mass %).

Furthermore, the logarithmic standard deviation $\sigma\zeta$, which indicates the narrowness of the particle diameter distribution, is favorably in the range of 0.1 to 0.46, more favorably 0.1 to 0.44, still more favorably 0.1 to 0.42, particularly favorably 0.1 to 0.40. The case where the logarithmic standard deviation $\sigma\zeta$ is less than 0.1 is unpractical because the productivity is greatly deteriorated. And the case where the logarithmic standard deviation $\sigma\zeta$ is more than 0.46 is unfavorable in that there remarkably occur problems of such as segregation.

The bulk density of the water-absorbent resin particles as obtained in the above way changes variously according to true density (g/cm$^3$) which is unambiguously determined by the monomer composition one by one. However, for example, when the water-absorbent resin is a poly(sodium acrylate), particularly, that which has a neutralization degree of 50 to 90 mol %, preferably 60 to 80 mol %, then its bulk density is usually favorably not less than 0.63 g/ml, more favorably not less than 0.65 g/ml. Incidentally, the bulk density may be measured with the apparatus according to JIS K-3362.

After the above pulverization, coarse particles (e.g. 850-μm-on product) or fine powders (e.g. 150-μm-passed product) may be recycled fitly as the case may be. The coarse particles may be re-pulverized, and the fine particles may be removed or recovered, thus adjusting the particle diameter distribution into the aforementioned range. Methods for recycling the fine powders of water-absorbent resins are, for example, disclosed in U.S. Pat. Nos. 4,950,692, 5,064,582, 5,264,495, 5,478,879, EP 0812873, EP 0885917, and EP 0844270. The amount of the fine powders being recycled is favorably not larger than 15 mass %, more favorably in the range of 1 to 10 mass %, still more favorably 2 to 8 mass %, of the entirety.

As to the water-absorbent resin particles as obtained in the above way, their absorption capacity without load (CRC) for a 0.90 mass % aqueous sodium chloride solution (physiological saline solution) is favorably not less than 5 g/g, more favorably not less than 10 g/g, still more favorably not less than 15 g/g, particularly favorably not less than 20 g/g, under conditions where the neutralization degree is not less than 50%, though being difficult to sweepingly express, because of (as demonstrated in the below-mentioned Referential Example 1) greatly changing dependently on the neutralization degree.

The water-absorbent resin particles, as obtained in the above way, favorably have an extractable component content of not higher than 50 mass %, more favorably not higher than 40 mass %, still more favorably not higher than 30 mass %, particularly favorably not higher than 20 mass %, most favorably not higher than 15 mass %.

The water-absorbent resin, used in the present invention, may be a water-absorbent resin having been obtained in the above way, but is favorably a water-absorbent resin having been obtained by a process including the step of surface-crosslink-treating the surfaces of the water-absorbent resin particles (having been obtained in the above way) with a surface-crosslinking agent.

As to the surface-crosslinked water-absorbent resin particles, their absorption capacity without load (CRC) for a 0.90 mass % aqueous sodium chloride solution (physiological saline solution) is favorably not less than 5 g/g, more favorably not less than 10 g/g, still more favorably not less than 15 g/g, particularly favorably not less than 20 g/g, under conditions where the neutralization degree is not less than 50%, though being difficult to sweepingly express, because of (as demonstrated in the below-mentioned Referential Example 1) greatly changing dependently on the neutralization degree.

The surface-crosslinked water-absorbent resin particles favorably have an extractable component content of not higher than 50 mass %, more favorably not higher than 40 mass %, still more favorably not higher than 30 mass %, particularly favorably not higher than 20 mass %, most favorably not higher than 15 mass %.

The surface-crosslinked water-absorbent resin particles are favorably adjusted to specific particle diameters. As to these particle diameters, the content of particles having particle diameters of smaller than 850 μm but not smaller than 150 μm is favorably not lower than 90 mass %, more favorably not lower than 95 mass %, still more favorably not lower than 97 mass %.

The mass-average particle diameter of the surface-crosslinked water-absorbent resin particles as obtained in the above way is determined according to purposes. However, favorably for sufficiently exercising the effects of the present invention, the mass-average particle diameter (D50) is in the range of 300 to 700 μm, more favorably 310 to 700 μm, still more favorably 320 to 700 μm, yet still more favorably 330 to 700 μm, yet still more favorably 340 to 700 μm, yet still more favorably 360 to 700 μm, yet still more favorably 380 to 700 μm, particularly favorably 400 to 700 μm.

In addition, the content of the surface-crosslinked water-absorbent resin particles having particle diameters of smaller than 150 μm is favorably in the range of 0 to 10 mass % (but not including 10 mass %), more favorably 0 to 7 mass % (but not including 7 mass %), still more favorably 0 to 5 mass % (but not including 5 mass %), particularly favorably 0 to 3 mass % (but not including 3 mass %).

Furthermore, the logarithmic standard deviation σζ, which indicates the narrowness of the particle diameter distribution, is favorably in the range of 0.1 to 0.46, more favorably 0.1 to 0.44, still more favorably 0.1 to 0.42, particularly favorably 0.1 to 0.40. The case where the logarithmic standard deviation σζ is less than 0.1 is unpractical because the productivity is greatly deteriorated. And the case where the logarithmic standard deviation σζ is more than 0.46 is unfavorable in that there remarkably occur problems of such as segregation.

As examples of surface-crosslinking agents usable in the present invention, there can be cited compounds which have at least two functional groups reactable with a functional group of the water-absorbent resin (wherein the at least two functional groups are, favorably, functional groups which can make a dehydration reaction or transesterification reaction with a carboxyl group). The functional group of the water-absorbent resin is favorably an anionic dissociating group and more favorably the carboxyl group.

Examples of the surface-crosslinking agent include: polyhydric alcohol compounds (e.g. ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol, and sorbitol); epoxy compounds (e.g. ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol); polyamine compounds (e.g. ethylenediamine, diethylenetriamine, triethylenetetramine, tetraethylenepentamine, pentaethylenehexamine, and polyethylenimine) and their inorganic or organic salts (e.g. azetidinium salts); polyisocyanate compounds (e.g. 2,4-tolylene diisocyanate and hexamethylene diisocyanate); aziridine compounds (e.g. polyaziridine); polyoxazoline compounds (e.g. 1,2-ethylenebisoxazoline, bisoxazoline, and polyoxazoline); carbonic acid derivatives (e.g. urea, thiourea, guanidine, dicyandiamide, 2-oxazolidinone); alkylene carbonate compounds (e.g. 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, and 1,3-dioxopan-2-one); haloepoxy compounds (e.g. epichlorohydrin, epibromohydrin, and α-methylepichlorohydrin) and their polyamine addition products (e.g. Kymene (registered trademark) produced by Hercules); oxetane compounds; silane coupling agents (e.g. γ-glycidoxypropyltrimethoxysilane and γ-aminopropyltriethoxysilane); and polyvalent metallic compounds (e.g. hydroxides or chlorides or sulfates or nitrates or carbonates of such as zinc, calcium, magnesium, aluminum, iron and zirconium). These may be used either alone respectively or in combinations with each other.

The amount of the surface-crosslinking agent as used is favorably in the range of 0.001 to 10 mass parts, more favorably 0.01 to 5 mass parts, per 100 mass parts of the water-absorbent resin particles. In the case where the amount of the surface-crosslinking agent as used is larger than 10 mass parts, not only are there economical disadvantages in that no performance corresponding thereto is obtained, but also the surface-crosslinking agent remains unfavorably in a large amount. In the case where the amount of the surface-crosslinking agent as used is smaller than 0.001 mass part, there is a possibility that no sufficient absorption performances can be exercised.

Such as inorganic acids and organic acids may be used in order to more accelerate the reaction with the surface-crosslinking agent to thus more enhance the absorption properties. Examples of these inorganic acids and organic acids include sulfuric acid, phosphoric acid, hydrochloric acid, citric acid, glyoxylic acid, glycolic acid, glycerol phosphate, glutaric acid, cinnamic acid, succinic acid, acetic acid, tartaric acid, lactic acid, pyruvic acid, fumaric acid, propionic acid, 3-hydroxypropionic acid, malonic acid, butyric acid, isobutyric acid, imidinoacetic acid, malic acid, isethionic acid, citraconic acid, adipic acid, itaconic acid, crotonic acid, oxalic acid, salicylic acid, gallic acid, sorbic acid, gluconic acid, and p-toluenesulfonic acid. In addition, there may be used those which are disclosed in EP 0668080, such as inorganic acids, organic acids, and polyamino acids. The amount of these materials as used differs according to such as pH of the water-absorbent resin, but is favorably in the range of 0 to 10 mass parts, more favorably 0.1 to 5 mass parts, per 100 mass parts of the water-absorbent resin particles.

When the water-absorbent resin particles and the surface-crosslinking agent are mixed together, water is favorably used as a solvent. The amount of water, as used, depends upon such as type or particle diameters of the water-absorbent resin particles, but is favorably larger than 0 mass part but not larger than 20 mass parts, more favorably in the range of 0.5 to 10 mass parts, still more favorably 0.5 to 5 mass parts, per 100 mass parts of the solid components of the water-absorbent resin particles.

When the water-absorbent resin particles and the surface-crosslinking agent are mixed together, a hydrophilic organic solvent may be used as a solvent, if necessary. Examples of the hydrophilic organic solvent include: lower alcohols (e.g. methyl alcohol, ethyl alcohol, n-propyl alcohol, isopropyl alcohol, n-butyl alcohol, isobutyl alcohol, and t-butyl alcohol); ketones (e.g. acetone); ethers (e.g. dioxane, tetrahydrofuran, and alkoxypolyethylene glycols); amides (e.g. N,N-dimethylformamide); and sulfoxides (e.g. dimethyl sulfoxide). The amount of the hydrophilic organic solvent, as used, depends upon such as type or particle diameters of the water-absorbent resin particles, but is favorably not larger than 20 mass parts, more favorably not larger than 10 mass parts, still more favorably not larger than 5 mass parts, per 100 mass parts of the solid components of the water-absorbent resin particles. When the water-absorbent resin particles and the surface-crosslinking agent are mixed together, there may be caused to coexist a noncrosslinkable water-soluble inorganic base (favorably,: alkaline metal salts, ammonium salts, alkaline metal hydroxides, and ammonia or its hydroxide) and/or an irreducible alkaline-metal-salt pH buffer (favorably such as hydrogencarbonates, dihydrogenphosphates, and hydrogenphosphates) for the purpose of more uniformly mixing the water-absorbent resin particles and the surface-crosslinking agent together. The amount of these materials, as used, depends upon such as type or particle diameters of the water-absorbent resin particles, but is favorably in the range of 0.005 to 10 mass parts, more favorably 0.05 to 5 mass parts, per 100 mass parts of the solid components of the water-absorbent resin particles.

When the water-absorbent resin particles are mixed with the surface-crosslinking agent, for example, there may be used a method in which: the water-absorbent resin particles are dispersed into the above hydrophilic organic solvent, and then the surface-crosslinking agent is added to the resultant dispersion. However, in a favorable method, the surface-crosslinking agent, which is dissolved or dispersed in water and/or the hydrophilic organic solvent if necessary, is spraywise or dropwise added directly to the water-absorbent resin particles under stirring. In addition, when the mixing is carried out with water, there may be made to coexist such as a water-insoluble inorganic fine particle powder, a water-soluble polyvalent metal, or a surfactant.

A mixing apparatus, as used when the water-absorbent resin particles and the surface-crosslinking agent are mixed together, has great mixing power favorably for uniformly and surely mixing both. Favorable examples of the mixing apparatus include cylinder type mixers, double-wall cone type mixers, V-character-shaped mixers, ribbon type mixers, screw type mixers, fluidized-furnace rotary disk type mixers, gas current type mixers, twin-arm kneaders, internal mixers, pulverizing type kneaders, rotary mixers, Lödige Mixer, and screw type extruders.

After the water-absorbent resin particles and the surface-crosslinking agent have been mixed together, the heat treatment and/or light irradiation treatment is carried out, whereby surfaces of the water-absorbent resin particles are crosslinked. When the heat treatment is carried out, the treating time is favorably in the range of 1 to 180 minutes, more favorably 3 to 120 minutes, still more favorably 5 to 100 minutes. The treating temperature is favorably in the range of 60 to 250° C., more favorably 100 to 210° C., still more favorably 120 to 200° C. In the case where the heat treatment temperature is lower than 60° C., there is a possibility not only that the heat treatment may take so much time as to cause the lowering of the productivity, but also that no uniform crosslinking may be achieved and therefore no objective particulate water-absorbent resin composition can be obtained. In addition, in the case where the heat treatment temperature is higher than 250° C., there is a case where: the water-absorbent resin particles are damaged and it is therefore difficult to obtain what is excellent in the water absorption properties.

The heat treatment can be carried out with conventional dryers or heating furnaces. Examples of the dryers include channel type mixing dryers, rotary dryers, disk dryers, fluidized-bed dryers, air blow type dryers, and infrared dryers.

In the case where the light irradiation treatment is carried out, it is favorable to irradiate ultraviolet rays, and besides, photoinitiators are usable.

In the case where the water-absorbent resin particles have been heated in the surface-crosslinking treatment, it is favorable to cool the heated water-absorbent resin particles. It is favorable that the cooling is carried out until the temperature falls into the range of 100 to 20° C. In addition, examples of coolers as used for the cooling include apparatuses in which the heating media of the above dryers as used for the heat treatment are replaced with cooling media.

The water-absorbent resin, used in the present invention, may be an agglomerated one.

It is meant by the agglomeration that a plurality of particles are agglomerated and fixed to each other to thereby make them form particles larger than the original particles. Typical agglomerated particles are agglomerated beads and broccoli-like as illustrated in FIG. 1 on page 75 of NONWOVENS WORLD October-November 2000 (published by Marketing Technology Service, Inc.). However, as to the agglomeration as referred to in the present invention, it is enough that the above agglomerated particles are formed partly in the water-absorbent resin or water-absorbent resin composition. Thus, all particles don't need to form the shape of the agglomerated particles. If the water-absorbent resin composition is subjected to the agglomeration treatment to thereby partly form the agglomerated water-absorbent resin particles, then minute fine particles can be decreased to thus enhance the handling facility. That is to say, it is favorable that the particulate water-absorbent resin composition partly comprises the agglomerated water-absorbent resin particles formed by the agglomeration treatment.

For the agglomeration, it will do to appropriately adopt hitherto publicly known methods such as disclosed in such as JP-A-097333/1986 (Kokai) and JP-A-313043/1994 (Kokai). Examples thereof include methods in which the agglomeration is carried out by dropwise or spraywise mixing the water-absorbent resin particles with water, aqueous solutions of organic solvents miscible with water, or aqueous solutions of water-soluble polymers under fluidizing and stirring. Above all, the agglomeration with water is favorable for not damaging the water absorption properties of the resultant water-absorbent resin.

Examples of the organic solvents miscible with water include: lower alcohols; lower glycols; monoethers between ethylene glycol and the lower alcohols; glycerol; and acetone.

Examples of the water-soluble polymers include: poly(acrylic acid); metal salts of poly(acrylic acid); carboxymethyl cellulose; polyethylene glycol; and polyvinyl alcohol. When the water-soluble polymers are used, it is favorable from the viewpoint of the preparation and conveyance of their aqueous solutions that the concentrations of their aqueous solutions are adjusted to not higher than 10 mass %.

The amount of the water or aqueous solution being used by being added to the water-absorbent resin particles is favorably in the range of 1 to 30 mass % relative to the water-absorbent resin particles. In the case where this amount is smaller than 1 mass %, there are disadvantages in that no sufficient agglomeration effect is obtained. In the case where this amount is larger than 30 mass %, there are disadvantages in that particles having too large particle diameters are unfavorably formed.

A mixing apparatus, as favorably used to carry out the agglomeration, has great mixing power favorably for carrying out uniform and sure mixing. Favorable examples thereof include cylinder type mixers, double-wall cone type mixers, V-character-shaped mixers, ribbon type mixers, screw type mixers, fluidized-furnace rotary disk type mixers, gas current type mixers, twin-arm kneaders, internal mixers, pulverizing type kneaders, rotary mixers, and screw type extruders.

Such agglomeration enables the exercise of effects such as: reduction of fine particle content; and prevention of dust generation.

[Particulate Water-absorbent Resin Composition]:

The particulate water-absorbent resin composition according to the present invention is a particulate water-absorbent resin composition comprising the carboxyl-group-containing water-absorbent resin as a main component.

The particulate water-absorbent resin composition according to the present invention comprises the carboxyl-group-containing water-absorbent resin as a main component, wherein the main component refers to a case where the content of the carboxyl-group-containing water-absorbent resin in the solid components of the particulate water-absorbent resin composition is favorably in the range of 80 to 100 mass %, more favorably 85 to 100 mass %, still more favorably 90 to 100 mass %, particularly favorably 95 to 100 mass %.

The content of particles having particle diameters (specific particle diameters) in the range of 300 to 600 µm (but not including 600 µm) in the particulate water-absorbent resin composition according to the present invention is favorably not lower than 40 mass %, more favorably not lower than 50 mass %, still more favorably not lower than 55 mass %. If the content of the particles having particle diameters (specific particle diameters) in the range of 300 to 600 µm (but not including 600 µm) in the particulate water-absorbent resin composition is in the above range, then the mass-average particle diameter comes in the range of 300 to 600 µm (but not including 600 µm), so the particles having particle diameters in the range of 300 to 600 µm (but not including 600 µm) can be judged to be particle diameters which represent the particulate water-absorbent resin composition.

The particulate water-absorbent resin composition according to the present invention is favorably not less than 20 g/g, more favorably not less than 25 g/g, still more favorably not less than 30 g/g, in specific-particle-diameter absorption capacity under load (0.01 psi (0.069 kPa), 1 hour). In addition, as to the upper limit value, this absorption capacity is not more than 60 g/g from the viewpoint of the balance between the production easiness and the performance.

The particulate water-absorbent resin composition according to the present invention is favorably not less than 20 g/g, more favorably not less than 21 g/g, still more favorably not less than 22 g/g, yet still more favorably not less than 23 g/g, yet still more favorably not less than 24 g/g, particularly favorably not less than 25 g/g, in specific-particle-diameter absorption capacity under load (0.29 psi (2.00 kPa), 1 hour). In addition, as to the upper limit value, this absorption capacity is not more than 60 g/g from the viewpoint of the balance between the production easiness and the performance.

The particulate water-absorbent resin composition according to the present invention is favorably not less than 16 g/g, more favorably not less than 17 g/g, still more favorably not less than 18 g/g, yet still more favorably not less than 19 g/g, yet still more favorably not less than 20 g/g, yet still more favorably not less than 21 g/g, yet still more favorably not less than 22 g/g, yet still more favorably not less than 23 g/g, particularly favorably not less than 24 g/g, in specific-particle-diameter absorption capacity under load (0.57 psi (3.93 kPa), 1 hour). In addition, as to the upper limit value, this absorption capacity is not more than 60 g/g from the viewpoint of the balance between the production easiness and the performance.

As is explained in the below-mentioned detailed description of Examples of some preferred embodiments, the above specific-particle-diameter absorption capacity under load (0.01 psi (0.069 kPa), 1 hour), specific-particle-diameter absorption capacity under load (0.29 psi (2.00 kPa), 1 hour), and specific-particle-diameter absorption capacity under load (0.57 psi (3.93 kPa), 1 hour) are absorption capacities under specific loads (0.01 psi (0.069 kPa), 0.29 psi (2.00 kPa), and 0.57 psi (3.93 kPa)), which are measured with selection of the particulate water-absorbent resin composition having the specific particle diameters.

The specific-particle-diameter absorption index is an index shown as the sum of the above specific-particle-diameter absorption capacity under a load of 0.01 psi (0.069 kPa) and specific-particle-diameter absorption capacity under a load of 0.29 psi (2.00 kPa).

The particulate water-absorbent resin composition according to the present invention is favorably not less than 3 g/g, more favorably not less than 3.5 g/g, still more favorably not less than 4 g/g, yet still more favorably not less than 4.5 g/g, yet still more favorably not less than 5 g/g, yet still more favorably not less than 5.5 g/g, yet still more favorably not less than 6 g/g, yet still more favorably not less than 7 g/g, particularly favorably not less than 7.5 g/g, most favorably not less than 8 g/g, in specific-particle-diameter absorption index increment in 20 hours and/or 4 hours. In addition, as to the upper limit value, this increment is not more than 20 g/g from the viewpoint of the balance between the production easiness and the performance.

As is explained in the below-mentioned detailed description of Examples of some preferred embodiments, the above specific-particle-diameter absorption index increment is an absorption index increment with the passage of time since after 1 hour, which are measured with selection of the particulate water-absorbent resin composition having the specific particle diameters.

The particulate water-absorbent resin composition according to the present invention is favorably not less than 20 g/g, more favorably not less than 25 g/g, still more favorably not less than 30 g/g, in absorption capacity under load (0.06 psi (0.41 kPa), 1 hour). In addition, as to the upper limit value, this absorption capacity is not more than 60 g/g from the viewpoint of the balance between the production easiness and the performance.

The particulate water-absorbent resin composition according to the present invention is favorably not less than 20 g/g, more favorably not less than 21 g/g, still more favorably not less than 22 g/g, yet still more favorably not less than 23 g/g, yet still more favorably not less than 24 g/g, particularly favorably not less than 25 g/g, in absorption capacity under load (0.3 psi (2.06 kPa), 1 hour). In addition, as to the upper limit value, this absorption capacity is not more than 60 g/g from the viewpoint of the balance between the production easiness and the performance.

The particulate water-absorbent resin composition according to the present invention is favorably not less than 15 g/g, more favorably not less than 16 g/g, still more favorably not less than 17 g/g, yet still more favorably not less than 18 g/g, yet still more favorably not less than 19 g/g, particularly favorably not less than 20 g/g, in absorption capacity under load (0.7 psi (4.83 kPa), 1 hour). In addition, as to the upper limit value, this absorption capacity is not more than 60 g/g from the viewpoint of the balance between the production easiness and the performance.

The particulate water-absorbent resin composition according to the present invention is favorably not less than 3 g/g, more favorably not less than 3.5 g/g, still more favorably not less than 4 g/g, yet still more favorably not less than 4.5 g/g, yet still more favorably not less than 5 g/g, yet still more favorably not less than 5.5 g/g, yet still more favorably not less than 6 g/g, yet still more favorably not less than 7 g/g, particularly favorably not less than 7.5 g/g, most favorably not less than 8 g/g, in absorption index increment in 20 hours and/or 4 hours. In addition, as to the upper limit value, this increment is not more than 20 g/g from the viewpoint of the balance between the production easiness and the performance.

The absorption index is an index shown as the sum of the above absorption capacity under a load of 0.06 psi (0.41 kPa) and absorption capacity under a load of 0.3 psi (2.06 kPa).

As is explained in the below-mentioned detailed description of Examples of some preferred embodiments, the above absorption index increment is an absorption index increment with the passage of time since after 1 hour.

The particulate water-absorbent resin composition according to the present invention, favorably, has a relation of (absorption capacity without load (1 hour))+3≧(specific-particle-diameter absorption capacity under load (0.29 psi (2.00 kPa), 1 hour))≧20 g/g between the absorption capacity without load (1 hour) and the specific-particle-diameter absorption capacity under load (0.29 psi (2.00 kPa), 1 hour).

The particulate water-absorbent resin composition according to the present invention, favorably, has a relation of (absorption capacity without load (1 hour))+3≧(absorption capacity under load (0.3 psi (2.06 kPa), 1 hour))≧20 g/g between the absorption capacity without load (1 hour) and the absorption capacity under load (0.3 psi (2.06 kPa), 1 hour).

The particulate water-absorbent resin composition according to the present invention is favorably not less than 15 g/g, more favorably not less than 20 g/g, still more favorably not less than 25 g/g, particularly favorably not less than 30 g/g, most favorably not less than 35 g/g, in absorption capacity without load (1 hour). In addition, as to the upper limit value, this absorption capacity is not more than 60 g/g from the viewpoint of the balance between the production easiness and the performance.

As to the particulate water-absorbent resin composition according to the present invention, its mass-average particle diameter is favorably in the range of 300 to 700 μm, more favorably 320 to 700 μm, still more favorably 340 to 700 μm, yet still more favorably 360 to 700 μm, yet still more favorably 380 to 700 μm, particularly favorably 400 to 700 μm.

In the particulate water-absorbent resin composition according to the present invention, the content of particles having particle diameters of smaller than 150 μm is favorably in the range of 0 to 10 mass % (but not including 10 mass %), more favorably 0 to 7 mass % (but not including 7 mass %), still more favorably 0 to 5 mass % (but not including 5 mass %), particularly favorably 0 to 3 mass % (but not including 3 mass %). The aforementioned particles having particle diameters of smaller than 150 μm are, favorably, water-absorbent resin particles.

The particulate water-absorbent resin composition according to the present invention, favorably, has the above properties. As particularly favorable combinations, there are cited the following first and second particulate water-absorbent resin compositions according to the present invention.

That is to say, the first particulate water-absorbent resin composition according to the present invention is a particulate water-absorbent resin composition comprising a carboxyl-group-containing water-absorbent resin in an amount of not smaller than 80 mass %, with the composition being characterized by being: not less than 20 g/g in specific-particle-diameter absorption capacity under load (0.29 psi (2.00 kPa), 1 hour); and not less than 3 g/g in specific-particle-diameter absorption index increment in 20 hours and/or 4 hours.

In addition, the second particulate water-absorbent resin composition according to the present invention is a particulate water-absorbent resin composition comprising a carboxyl-group-containing water-absorbent resin in an amount of not smaller than 80 mass %, with the composition being characterized by being: in the range of 320 to 700 μm in mass-average particle diameter; not less than 20 g/g in absorption capacity under load (0.3 psi (2.06 kPa), 1 hour); and not less than 3 g/g in absorption index increment in 20 hours and/or 4 hours.

In addition, the particulate water-absorbent resin composition according to the present invention, favorably, has a relation of (absorption capacity without load (1 hour))+3≧(specific-particle-diameter absorption capacity under load (0.29 psi (2.00 kPa), 1 hour))≧20 g/g and is not less than 3 g/g in specific-particle-diameter absorption index increment in 20 hours and/or 4 hours.

In addition, the particulate water-absorbent resin composition according to the present invention, favorably, is in the range of 320 to 700 μm in mass-average particle diameter and has a relation of (absorption capacity without load (1 hour))+3≧(absorption capacity under load (0.3 psi (2.06 kPa), 1 hour))≧20 g/g and is not less than 3 g/g in absorption index increment in 20 hours and/or 4 hours.

Because of having such specific properties (e.g. absorption properties, mass-average particle diameter), the particulate water-absorbent resin composition according to the present invention can sufficiently exercise the effects of the present invention.

As to the particulate water-absorbent resin composition according to the present invention, its production process is not especially limited. However, examples thereof include the following production processes 1 to 3.

Production process 1: a process in which at least two water-absorbent resins having different neutralization degrees in specific ranges are mixed together under a specific range of condition (the below-mentioned neutralization degree-absorption capacity-mixing index).

Production process 2: a process in which at least two water-absorbent resins having different neutralization degrees in specific ranges are mixed together under a specific range of condition (the below-mentioned neutralization degree-particle diameters-absorption capacity-mixing index).

Production process 3: a process in which a water-absorbent resin having a controlled low neutralization degree is surface-crosslinked and then mixed with a substance capable of neutralizing the carboxyl group (e.g. sodium (hydrogen) carbon ate).

Favorable ones of the above production processes 1 to 3 are the production processes 1 and 2. Hereinafter, these production processes 1 and 2 are cited as favorable examples to give further descriptions about the particulate water-absorbent resin composition according to the present invention.

As an example for obtaining the particulate water-absorbent resin composition according to the present invention, it is favorable that this composition comprises a carboxyl-group-containing water-absorbent resin (A) of not less than 50% in neutralization degree of the carboxyl groups and a carboxyl-group-containing water-absorbent resin (B) of less than 50% in neutralization degree of the carboxyl groups in a mass ratio of (A):(B)=90:10 to 10:90, wherein there is a difference of not less than 30% between the neutralization degrees of the carboxyl-group-containing water-absorbent resins (A) and (B).

Each of the carboxyl-group-containing water-absorbent resins (A) and (B) may be either one kind of carboxyl-group-containing water-absorbent resin or a mixture of at least two kinds of carboxyl-group-containing water-absorbent resins.

When the carboxyl-group-containing water-absorbent resin (A) is the mixture of at least two kinds of carboxyl-group-containing water-absorbent resins, it will do that the average neutralization degree, as calculated from respective neutralization degrees and mixing ratios of the carboxyl-group-containing water-absorbent resins contained in the mixture, is not less than 50%. When the carboxyl-group-containing water-absorbent resin (B) is the mixture of at least two kinds of carboxyl-group-containing water-absorbent resins, it will do that the average neutralization degree, as calculated from respective neutralization degrees and mixing ratios of the carboxyl-group-containing water-absorbent resins contained in the mixture, is less than 50%. For example, in the case of a mixture in which a carboxyl-group-containing water-absorbent resin of X % in neutralization degree of the carboxyl groups and a carboxyl-group-containing water-absorbent resin of Y % in neutralization degree of the carboxyl groups are mixed together in a ratio of 1:2, the calculation is made as follows:

Average neutralization degree (%)=$X \times 1/3 + Y \times 2/3$

When the water-absorbent resins different from each other in neutralization degree is already in the mixed state, it is possible that the metal ion content and ammonium ion content of each particle are examined with an electron probe X-ray microanalyzer (EPMA) and/or an energy-dispersive type X-ray spectrometer (EDS) to thus determine the neutralization degrees and the mixing ratios.

As to the setting of the neutralization degree of the carboxyl-group-containing water-absorbent resin (A), this neutralization degree is favorably set in the range of 50 to 100%, but is more favorably in the range of 60 to 100%, still more favorably 70 to 100%.

The setting of the neutralization degree of the carboxyl-group-containing water-absorbent resin (B) is important in point of exercising a great influence on the specific-particle-diameter absorption index increment, and this neutralization degree is favorably set in the range of 0 to 50% (but not including 50%), but is more favorably in the range of 0 to 30% (but not including 30%), still more favorably 0 to 25% (but not including 25%), yet still more favorably 0 to 20% (but not including 20%), particularly favorably 0 to 15% (but not including 15%), most favorably 0 to 10% (but not including 10%).

As to the carboxyl-group-containing water-absorbent resins (A) and (B), it is favorable that at least either one of them is a surface-treated one, particularly, a surface-crosslink-treated one, and it is more favorable that both of them are surface-treated ones, particularly, surface-crosslink-treated ones. When the carboxyl-group-containing water-absorbent resins (A) and/or (B) are the mixtures of at least two kinds of carboxyl-group-containing water-absorbent resins, it is favorable that at least one kind of carboxyl-group-containing water-absorbent resin is the surface-treated one, and it is more favorable that all the carboxyl-group-containing water-absorbent resins are the surface-treated ones.

The particulate shapes of the carboxyl-group-containing water-absorbent resins (A) and (B) may be either irregular pulverized ones or spherical ones, and also may be mixtures of irregular pulverized particles and spherical particles.

It is favorable that the carboxyl-group-containing water-absorbent resins (A) and/or (B) are agglomerated ones. When the carboxyl-group-containing water-absorbent resins (A) and/or (B) are the mixtures of at least two kinds of carboxyl-group-containing water-absorbent resins, it is favorable that at least one kind of carboxyl-group-containing water-absorbent resin is the agglomerated one, and it is more favorable that all the carboxyl-group-containing water-absorbent resins are the agglomerated ones. Favorable agglomeration methods are such methods as specified as the aforementioned agglomeration methods.

The mass ratio between the carboxyl-group-containing water-absorbent resins (A) and (B) is in the range of (A):(B)=90:10 to 10:90. The mass ratio between the carboxyl-group-containing water-absorbent resins (A) and (B) will do if it is in this range. It is impossible to sweepingly specify its more optimum range, because it depends on what neutralization degrees the carboxyl-group-containing water-absorbent resins (A) and (B) have. However, as a rough tendency, it is favorably in the range of (A):(B)=85:15 to 15:85, more favorably (A):(B)=80:20 to 20:80, still more favorably (A):(B)=80:20 to 40:60, yet still more favorably (A):(B)=80:20 to 50:50.

In the particulate water-absorbent resin composition according to the present invention, it is favorable that there is a difference of not less than 30% between the neutralization degrees of the carboxyl-group-containing water-absorbent resins (A) and (B). If the difference in neutralization degree between the carboxyl-group-containing water-absorbent resin (A) having a higher neutralization degree of the carboxyl groups and the carboxyl-group-containing water-absorbent resin (B) having a lower neutralization degree of the carboxyl groups is made large in this way, then the absorption ability in an initial short time is secured in some degree, and further, the absorption capacity lastingly increases over a long period, and also the liquid permeability and the liquid diffusibility can be secured.

Incidentally, the liquid permeability and the liquid diffusibility, which are referred to in the present invention, indicate the mobility and permeability of liquids through spaces between water-absorbent resin gel particles and also indicate the ability to take liquids into water-absorbent articles such as disposable diapers. More specifically, examples of indexes to indicate the mobility and permeability of liquids through spaces between water-absorbent resin gel particles include: absorption capacity under load and specific-particle-diameter absorption capacity under load (these absorption capacities are recited in the below-mentioned detailed description of Examples of some preferred embodiments); and further, "saline flow conductivity test (SFC)" (as described in Pamphlet of WO 95/22356); and "liquid-passing time of saline" (as described in JP-A-057010/1994 (Kokai)). Examples of indexes to indicate the ability to take liquids into water-absorbent articles such as disposable diapers include a liquid intake time into disposable diapers (this time is recited in the below-mentioned detailed description of Examples of some preferred embodiments).

From the present inventors' study, there is inferred the following principle on which: in the present invention, when the difference between the neutralization degrees of the carboxyl-group-containing water-absorbent resins (A) and (B) is set at not less than 30%, then there are exercised the effects of the present invention such that: the absorption ability in an initial short time is secured in some degree, and further, the absorption capacity lastingly increases over a long period, and also the liquid permeability and the liquid diffusibility can be secured.

As is demonstrated in the below-mentioned Referential Example 1, there is seen a peculiar phenomenon such that: although the absorption capacity of the carboxyl-group-containing water-absorbent resin increases with the increase of the neutralization. degree, the extent of this increase of the absorption capacity is not constant, but the extent of the increase of the absorption capacity due to the increase of the neutralization degree is sharp until the neutralization degree reaches about 50%, and then the extent of the increase of the absorption capacity due to the increase of the neutralization degree becomes gentle if the neutralization degree increases to not less than about 50%.

On the other hand, when the carboxyl-group-containing water-absorbent resin (A) of not less than 50% in neutralization degree of the carboxyl groups and the carboxyl-group-containing water-absorbent resin (B) of less than 50% in neutralization degree of the carboxyl groups coexist like in the particulate water-absorbent resin composition according to the present invention, then there can be considered to occur "ion transfer" such that counter-cations (e.g. Na ions), which neutralize carboxyl groups, transfer between the carboxyl-group-containing water-absorbent resins (A) and (B) in order to equalize their neutralization degrees by the driving force as generated by the difference in pH between the carboxyl-group-containing water-absorbent resins (A) and (B).

Accordingly, the neutralization degree of the carboxyl-group-containing water-absorbent resin (A), originally having a high absorption capacity because of not being less than 50% in neutralization degree of the carboxyl groups, gradually decreases, while the neutralization degree of the carboxyl-group-containing water-absorbent resin (B) of less than 50% in neutralization degree of the carboxyl groups, gradually increases. From this, it follows that a slow absorption rate is produced and further that an increase of the absorption capacity with the passage of time is produced. The effects of the present invention can be considered to be produced as a result of it.

In the particulate water-absorbent resin composition according to the present invention, it is favorable that there is a difference of not less than 30% between the neutralization degrees of the carboxyl-group-containing water-absorbent resins (A) and (B). However, the securing itself of the difference of at least 30% is important, and the effects of the present invention are not necessarily produced increasingly as the difference between the neutralization degrees increases from 30%. The reason for this is that the optimum range of the difference between the neutralization degrees depends also on how there are selected the following: the mass ratio between the carboxyl-group-containing water-absorbent resins (A) and (B); and the particle diameters, particle diameter distributions, fine powder contents, and further the absorption performances under the neutralization, of the carboxyl-group-containing water-absorbent resins (A) and (B). However, as a rough tendency, the difference between the neutralization degrees of the carboxyl-group-containing water-absorbent resins (A) and (B) is favorably not less than 35%, more favorably not less than 40%, still more favorably not less than 50%, particularly favorably not less than 60%, most favorably not less than 65%.

Furthermore, an effective increase of the specific-particle-diameter absorption index (specific-particle-diameter absorption index increment) has been found to be produced when a relation of the following expression 1 is satisfied between the difference ($\Delta N$) of the carboxyl-group-containing water-absorbent resin (A) from the carboxyl-group-containing water-absorbent resin (B) in neutralization degree and the mixing ratio (ratio of the carboxyl-group-containing water-absorbent resin (A): $\alpha$).

$$\Delta N \times (0.5 - |0.5 - \alpha|) \geq 11 \quad \text{(expression 1)}$$

The left side of the above expression 1 is referred to as "neutralization degree-mixing index (NM index)".

Incidentally, the above $(0.5-|0.5-\alpha|)$ is a term as led from an experimental fact that the absorption index increment becomes maximum at a mixing ratio $\alpha=0.5$.

In the present invention, the neutralization degree-mixing index is favorably not less than 11, but is more favorably not less than 13, still more favorably not less than 15, yet still more favorably not less than 17, yet still more favorably not less than 19, yet still more favorably not less than 20, yet still more favorably not less than 21, yet still more favorably not less than 22, yet still more favorably not less than 23, yet still more favorably not less than 24, yet still more favorably not less than 25, particularly favorably not less than 27. In addition, as to the upper limit value, this index is not more than 50 from the viewpoint of the balance between the production easiness and the performance.

The specific-particle-diameter absorption index increment is relevant extremely closely to the neutralization degree-mixing index under specific-particle-diameter conditions of smaller than 600 μm but not smaller than 300 μm.

Furthermore, a more effective increase of the specific-particle-diameter absorption index (specific-particle-diameter absorption index increment) has been found to be produced when there is satisfied a relation of the following expression 2 considering the absorption properties of the water-absorbent resin composition.

$$\Delta N \times (0.5-|0.5-\alpha|) \times \text{specific-particle-diameter absorption capacity under load (0.30 psi (2.06 kPa), 1 hour)/absorption capacity without load (1 hour)} \geq 11 \quad \text{(expression 2)}$$

The left side of the above expression 2 is referred to as "neutralization degree-absorption capacity-mixing index (NCM index)".

As the absorption capacity under load (0.30 psi (2.06 kPa), 1 hour) in the above expression 2, the value of the specific-particle-diameter absorption capacity under load (0.29 psi (2.00 kPa), 1 hour) is used when the carboxyl-group-containing water-absorbent resins (A) and (B) are the same in particle diameter.

In the present invention, the neutralization degree-absorption capacity-mixing index is favorably not less than 11, but is more favorably not less than 13, still more favorably not less than 15, yet still more favorably not less than 17, yet still more favorably not less than 19, yet still more favorably not less than 20, yet still more favorably not less than 21, yet still more favorably not less than 22, yet still more favorably not less than 23, yet still more favorably not less than 24, yet still more favorably not less than 25, particularly favorably not less than 27. In addition, as to the upper limit value, this index is not more than 50 from the viewpoint of the balance between the production easiness and the performance.

The specific-particle-diameter absorption index increment is relevant extremely closely to the neutralization degree-absorption capacity-mixing index under specific-particle-diameter conditions of smaller than 600 μm but not smaller than 300 μm.

In addition, a more effective increase of the absorption index (absorption index increment) has been found to be produced when there is satisfied a relation of the following expression 3 in the case of considering the particle diameters of the water-absorbent resin composition.

$$\Delta N \times (0.5 - |0.5 - \alpha|) \times (d/d')^2 \times \text{absorption capacity under load (0.30 psi (2.06 kPa), 1 hour)/absorption capacity without load (1 hour)} \geq 11 \quad \text{(expression 3)}$$

The left side of the above expression 3 is referred to as "neutralization degree-particle diameters-absorption capacity-mixing index (NPCM index)".

Hereupon: d is an average particle diameter of the water-absorbent resin composition (when (A) and (B) are different in particle diameter, their average is applied); d' is an average particle diameter (450 μm) of particles having particle diameters of smaller than 600 μm but not smaller than 300 μm; and $(d/d')^2$ denotes a corrected value from the particulate surface area of the water-absorbent resin composition based on the particles having particle diameters of smaller than 600 μm but not smaller than 300 μm.

In the present invention, the neutralization degree-particle diameters-absorption capacity-mixing index is favorably not less than 11, but is more favorably not less than 13, still more favorably not less than 15, yet still more favorably not less than 17, yet still more favorably not less than 19, yet still more favorably not less than 20, yet still more favorably not less than 21, yet still more favorably not less than 22, yet still more favorably not less than 23, yet still more favorably not less than 24, yet still more favorably not less than 25, particularly favorably not less than 27. In addition, as to the upper limit value, this index is not more than 50 from the viewpoint of the balance between the production easiness and the performance.

As to the setting of the neutralization degree of the carboxyl-group-containing water-absorbent resin (A), this neutralization degree is favorably set at not less than 50%, but is more favorably not less than 60%, still more favorably not less than 70%.

The setting of the neutralization degree of the carboxyl-group-containing water-absorbent resin (B) is important in point of exercising a great influence on the absorption index increment, and this neutralization degree is favorably set at less than 50%, but is more favorably less than 30%, still more favorably less than 25%, yet still more favorably less than 20%, particularly favorably less than 15%, most favorably less than 10%.

In the particulate water-absorbent resin composition according to the present invention, it is favorable for achieving the lasting increase of the absorption capacity (specific-particle-diameter absorption index increment or absorption index increment) over a long period that the mass-average particle diameters of the carboxyl-group-containing water-absorbent resins (A) and (B) are set so as to satisfy specific conditions.

Specifically, it is favorable that at least either one of the carboxyl-group-containing water-absorbent resins (A) and (B) has a mass-average particle diameter of not smaller than 300 μm, more favorably not smaller than 320 μm, still more favorably not smaller than 340 μm, yet still more favorably not smaller than 360 μm, particularly favorably not smaller than 380 μm, most favorably not smaller than 400 μm.

Furthermore, it is more favorable that both of the carboxyl-group-containing water-absorbent resins (A) and (B) have a mass-average particle diameter of 300 to 700 μm, still more favorably 320 to 700 μm, yet still more favorably 340 to 700 μm, yet still more favorably 360 to 700 μm, particularly favorably 380 to 700 μm, most favorably 400 to 700 μm.

Furthermore, the logarithmic standard deviation σζ, which indicates the narrowness of the particle diameter distribution, is favorably in the range of 0.1 to 0.46, more favorably 0.1 to 0.44, still more favorably 0.1 to 0.42, particularly favorably 0.1 to 0.40. The case where the logarithmic standard deviation σζ is less than 0.1 is unpractical because the productivity is greatly deteriorated. And the case where the logarithmic standard deviation σζ is more than 0.46 is unfavorable in that there remarkably occur problems of such as segregation.

In the case where both of the carboxyl-group-containing water-absorbent resins (A) and (B), used in the present invention, have a mass-average particle diameter of smaller than 300 μm, the ion transfer may occur, but there is a possibility that: because the surface area is large, the speed of the ion transfer is so fast that the effect of the increase of the absorption capacity over a long period is small, thus resulting in making no great difference from such a case of one kind of water-absorbent resin as hitherto publicly known.

In the case where both of the carboxyl-group-containing water-absorbent resins (A) and (B), used in the present invention, have a mass-average particle diameter of larger than 700 μm, there is a possibility that there may occur problems such that the uses for such as diapers involve the texture deterioration.

There is no especial limitation on the process for production of the particulate water-absorbent resin composition according to the present invention. Examples thereof include: dry-blending or gel-blending of the carboxyl-group-containing water-absorbent resins (A) and (B); and mixing when hydrogel polymers are pulverized after having been dried in processes for production of the carboxyl-group-containing water-absorbent resins (A) and (B). However, favorable ones are the dry-blending and the gel-blending.

Examples of the dry-blending process include a process in which dried materials of the carboxyl-group-containing water-absorbent resins (A) and (B) are mixed together in a predetermined mixing ratio. A mixing apparatus has great mixing power favorably for carrying out uniform and sure mixing. Favorable examples thereof include cylinder type mixers, double-wall cone type mixers, V-character-shaped mixers, Lödige Mixer, ribbon type mixers, screw type mixers, fluidized-furnace rotary disk type mixers, gas current type mixers, twin-arm kneaders, internal mixers, pulverizing type kneaders, rotary mixers, and screw type extruders.

Examples of the gel-blending process include: a process in which pulverized hydrogels of the carboxyl-group-containing water-absorbent resins (A) and (B) (having been obtained separately by the aqueous solution polymerizations) are mixed together in a predetermined mixing ratio and then dried; and besides, as another process, a process in which hydrogels of the carboxyl-group-containing water-absorbent resins (A) and (B) (having been obtained separately by the aqueous solution polymerizations) are simultaneously supplied to a pulverizer such as meat chopper in a predetermined mixing ratio, and then mixed together while being pulverized, and then dried. Examples of machines for mixing and pulverizing the hydrogels include kneaders, meat choppers, and twin-screw type extruders.

By such gel-blending processes as mentioned above, the carboxyl-group-containing water-absorbent resins (A) and (B) can be produced with one drier, so the production efficiency can be enhanced.

As is aforementioned, in the particulate water-absorbent resin composition according to the present invention, it is favorable that at least either one of the carboxyl-group-containing water-absorbent resins (A) and (B) is surface-treated (favorably, surface-crosslink-treated), and it is more favorable that both of them are surface-treated (favorably, surface-crosslink-treated). Examples of processes therefor include: a process in which the carboxyl-group-containing water-absorbent resins (A) and (B) are separately surface-treated and then dry-blended together; and a process in which a mixture obtained by mixing the carboxyl-group-containing water-absorbent resins (A) and (B) together by the dry-blending process or a dried mixture of these water-absorbent resins obtained by the gel-blending process is surface-treated by the same method as the aforementioned surface treatment, thus simultaneously surface-treating the two kinds. Particularly, in the latter process, simultaneous surface treatment of the two kinds is carried out with one machine, so there is an advantage in that the production efficiency can be enhanced.

As is aforementioned, in the particulate water-absorbent resin composition according to the present invention, it is favorable that the carboxyl-group-containing water-absorbent resins (A) and (B) are agglomerated ones. Examples of processes therefor include: a process in which the carboxyl-group-containing water-absorbent resins (A) and (B) are separately agglomerated and then mixed together by the dry-blending process; a process in which a dried mixture obtained by the gel-blending process is agglomerated; and a process in which the carboxyl-group-containing water-absorbent resins (A) and (B) are agglomerated when being dry-blended together or thereafter. By carrying out any of these three processes, there is obtained an advantage such that the amount of the fine powder causing the dust generation can be reduced, with the result that the working environment is greatly improved. Particularly, the process in which the carboxyl-group-containing water-absorbent resins (A) and (B) are agglomerated when being dry-blended together or thereafter is favorable in that the carboxyl-group-containing water-absorbent resins (A) and (B) agglomerate together to form particles, with the result that: in the particulate water-absorbent resin composition according to the present invention, the uniformity of the mixed state (distributed state) of the carboxyl-group-containing water-absorbent resins (A) and (B) is enhanced, or segregation is prevented.

If necessary, the processes for production of the water-absorbent resin (used in the present invention) and the particulate water-absorbent resin composition (according to the present invention) may further comprise a step for providing the water-absorbent resin particles with various functions, for example, a step of adding such as: inorganic fine particles (e.g. fumed silica, kaolin, bentonite, calcium carbonate); deodorants; antibacterial agents; perfumes; foaming agents; pigments; dyes; hydrophilic short fibers; plasticizers; pressure-sensitive adhesives; metal soap; surfactants; manure; oxidants; reducing agents; water; salts; chelating agents; fungicides; hydrophilic polymers (e.g. polyethylene glycol); paraffins; hydrophobic polymers; thermoplastic resins (e.g. polyethylene, polypropylene); and thermosetting resins (e.g. polyester resins, urea resins). The amount of these additives as used is favorably in the range of 0 to 10 mass parts, more favorably 0 to 1 mass part, per 100 mass parts of the water-absorbent resin particles.

As to the form of the addition of the above additives, they are added in the form of aqueous solutions, suspensions, or powders. Examples of processes for the addition of the additives include: a process in which the above additives are added to the carboxyl-group-containing water-absorbent resins (A) and/or (B), and then they are mixed together by the dry-blending process, thus obtaining the particulate water-absorbent resin composition; a process in which the above additives are added to a dried mixture obtained by the gel-blending process; and a process in which the above additives are added when or after the carboxyl-group-containing water-absorbent resins (A) and (B) are dry-blended together.

When the particulate water-absorbent resin composition according to the present invention is obtained by the aforementioned production process 3 (process in which a water-absorbent resin having a controlled low neutralization degree is surface-crosslinked and then mixed with a substance capable of neutralizing the carboxyl group (e.g. sodium (hydrogen)carbonate)), then this composition is a particulate water-absorbent resin composition obtained by mixing the surface-crosslink-treated carboxyl-group-containing water-absorbent resin and the substance capable of neutralizing the carboxyl group. The content of the carboxyl-group-containing water-absorbent resin in this particulate water-absorbent resin composition is favorably in the range of 80 to 95 mass %, more favorably 80 to 90 mass %, still more favorably 80 to 85 mass %. In the case where the content of the carboxyl-group-containing water-absorbent resin in the above particulate water-absorbent resin composition is lower than 80 mass %, there is a possibility that the absorption properties in a short time may be deteriorated, thus it becoming impossible for the particulate water-absorbent resin composition according to the present invention to satisfy the physical properties (parameters) which this composition is to satisfy. In the case where the above content is higher than 95 mass %, there is a possibility that the increase of the absorption capacity with the passage of time may be insufficient, thus it becoming impossible for the particulate water-absorbent resin composition according to the present invention to satisfy the physical properties (parameters) which this composition is to satisfy.

The content of the substance capable of neutralizing the carboxyl group in the above particulate water-absorbent resin composition is favorably in the range of 5 to 20 mass %, more favorably 10 to 20 mass %, still more favorably 15 to 20 mass %. In the case where the content of the substance capable of neutralizing the carboxyl group in the above particulate water-absorbent resin composition is lower than 5 mass %, there is a possibility that the increase of the absorption capacity with the passage of time may be insufficient, thus it becoming impossible for the particulate water-absorbent resin composition according to the present invention to satisfy the physical properties (parameters) which this composition is to satisfy. In the case where the above content is higher than 20 mass %, there is a possibility that the absorption properties in a short time may be deteriorated, thus it becoming impossible for the particulate water-absorbent resin composition according to the present invention to satisfy the physical properties (parameters) which this composition is to satisfy.

The neutralization degree of the water-absorbent resin having a controlled low neutralization degree is favorably in the range of 0 to 70% (but not including 70%), more favorably 10 to 60% (but not including 60%), still more favorably 10 to 50% (but not including 50%), particularly favorably 20 to 40% (but not including 40%).

As the substance capable of neutralizing the carboxyl group, there is preferred what can be handled as a powder at room temperature. Examples thereof include alkaline metal carbonates such as sodium carbonate, sodium hydrogencarbonate, lithium carbonate, lithium hydrogencarbonate, potassium carbonate, and potassium hydrogencarbonate.

The mass-average particle diameter (D50) of the substance capable of neutralizing the carboxyl group is favorably in the range of 300 to 700 μm, more favorably 320 to 700 μm, still more favorably 340 to 700 μm, yet still more favorably 360 to 700 μm, yet still more favorably 380 to 700 μm, particularly favorably 400 to 700 μm.

The logarithmic standard deviation ($\sigma\zeta$) of the substance capable of neutralizing the carboxyl group is favorably in the range of 0.1 to 0.46, more favorably 0.1 to 0.44, still more favorably 0.1 to 0.42, particularly favorably 0.1 to 0.40. The case where the logarithmic standard deviation ($\sigma\zeta$) is less than 0.1 is unpractical because the productivity is greatly deteriorated. And the case where the logarithmic standard deviation ($\sigma\zeta$) is more than 0.46 is unfavorable in that there remarkably occur problems of such as segregation.

In the substance capable of neutralizing the carboxyl group, the content of particles having particle diameters of smaller than 150 μm is favorably in the range of 0 to 10 mass % (but not including 10 mass %), more favorably 0 to 7 mass % (but not including 7 mass %), still more favorably 0 to 5 mass % (but not including 5 mass %), particularly favorably 0 to 3 mass % (but not including 3 mass %).

As to processes for mixing the surface-crosslink-treated carboxyl-group-containing water-absorbent resin and the substance capable of neutralizing the carboxyl group, there is preferred a process in which they are dry-blended in a dry state. As to such a process, it is enough to carry out it in accordance with the aforementioned description about the dry-blending process.

[Water-absorbent Structure and Water-absorbent Article]:

The particulate water-absorbent resin composition according to the present invention can be combined with an appropriate material and thereby formed into the water-absorbent structure which is, for example, favorable as an absorbent layer for sanitary materials.

The water-absorbent structure refers to a molded composition which comprises the particulate water-absorbent resin composition and another material and is used for sanitary materials (e.g. disposable diapers, sanitary napkins, incontinent pads, and medical pads) for absorption of such as blood, body fluids, and urine.

Examples of the material, which is used in combination with the particulate water-absorbent resin composition, include cellulose fibers. Specific examples of the cellulose fibers include: wood pulp fibers from wood, such as mechanical pulp, chemical pulp, semichemical pulp, and dissolving pulp; and synthetic cellulose fibers, such as rayon and acetate. Favorable cellulose fibers are the wood pulp fibers. These cellulose fibers may partly contain synthetic fibers such as nylon and polyester. When the particulate water-absorbent resin composition according to the present invention is used as a portion of the water-absorbent structure, the mass ratio of the particulate water-absorbent resin composition according to the present invention as contained in the water-absorbent structure is favorably in the range of 20 to 100 mass %, more favorably 30 to 90 mass %. In the case where the mass ratio of the particulate water-absorbent resin composition according to the present invention as contained in the water-absorbent structure is smaller than 20 mass %, there is a possibility that no sufficient effects can be obtained.

For the purpose of obtaining the water-absorbent structure from the particulate water-absorbent resin composition and the cellulose fibers, for example, publicly known means for obtaining water-absorbent structures can appropriate be selected from among such as: a method in which the particulate water-absorbent resin composition is spread onto paper or mat made of the cellulose fibers and is, if necessary, interposed therebetween; and a method in which the cellulose fibers and the particulate water-absorbent resin composition are uniformly blended together. A favorable method is a method in which the particulate water-absorbent resin composition and the cellulose fibers are mixed together in a dry manner and then compressed. This method can prevent the particulate water-absorbent resin composition from falling off from the cellulose fibers. The compression is favorably carried out under heating, and its temperature range is favorably in the range of 50 to 200° C. For the purpose of obtaining the water-absorbent structure, methods as disclosed in JP-A-509591/1997 (Kohyo) and JP-A-290000/1997 (Kokai) are also favorably usable.

In the case where used for water-absorbent structures, the particulate water-absorbent resin composition according to the present invention is so good in the balance between the liquid permeability and the capillary suction force as to give water-absorbent structures which are very excellent in that they quickly take liquids in and further in that the amount of the liquids remaining on their surface layers is small.

Because the particulate water-absorbent resin composition according to the present invention has the excellent water absorption properties, this particulate water-absorbent resin composition can be used as water-absorbing and water-retaining agents for water-absorbent articles, namely, various purposes. For example, this composition can be used for such as: water-absorbing and water-retaining agents for absorbent articles (e.g. disposable diapers, sanitary napkins, incontinent pads, and medical pads); agricultural and horticultural water-retaining agents (e.g. substitutes for peat moss, soil-modifying-and-improving agents, water-retaining agents, and agents for duration of effects of agricultural chemicals); water-retaining agents for buildings (e.g. dew-condensation-preventing agents for interior wall materials, cement additives); release control agents; coldness-retaining agents; disposable portable body warmers; sludge-solidifying agents; freshness-retaining agents for foods; ion-exchange column materials; dehydrating agents for sludge or oil; desiccating agents; and humidity-adjusting materials. In addition, the particulate water-absorbent resin composition according to the present invention can be used particularly favorably for sanitary materials for absorption of excrement, urine, or blood, such as disposable diapers and sanitary napkins.

In the case where the water-absorbent structure obtained from the particulate water-absorbent resin composition according to the present invention is used for sanitary materials (e.g. disposable diapers, sanitary napkins, incontinent pads, and medical pads), this water-absorbent structure is used favorably with a constitution including: (a) a liquid-permeable top sheet placed so as to be adjacent to a wearer's body; (b) a liquid-impermeable back sheet placed so as to be adjacent to the wearer's clothes at a distance from the wearer's body; and (c) the water-absorbent structure placed between the top sheet and the back sheet. The water-absorbent structure may be in more than one layer or used along with such as a pulp layer.

In a more favorable constitution, the basis mass of the particulate water-absorbent resin composition in the water-absorbent structure is favorably in the range of 60 to 1,500 g/m$^2$, more favorably 100 to 1,000 g/m$^2$, still more favorably 200 to 800 g/m$^2$.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to them. Hereinafter, for convenience, the units "mass part(s) (weight part(s))" and "liter(s)" may be referred to simply as "part(s)" and "L" respectively. In addition, the unit "mass % (weight %)" may be referred to as "wt %".

The performances of the water-absorbent resin (which may hereinafter be referred to as water-absorbent resin particles) or particulate water-absorbent resin composition were measured by the following methods. The following measurement was carried out under conditions of a room temperature (25° C.) and a humidity of 50 RH %.

Incidentally, in cases of particulate water-absorbent resin compositions having been used for end products such as sanitary materials, these particulate water-absorbent resin compositions have already absorbed moisture. Therefore, the measurement may be carried out after a process including the steps of appropriately separating the particulate water-absorbent resin compositions from the end products and then drying the separated particulate water-absorbent resin compositions under a reduced pressure at a low temperature (e.g. under not higher than 1 mmHg at 60° C. for 12 hours).

All the water-absorbent resins and particulate water-absorbent resin compositions as used in the following Examples and Comparative Examples had water contents of not higher than 6 mass %.

The solution used to make it absorbed in the present invention is a 0.90 mass % aqueous sodium chloride solution which may be abbreviated to physiological saline solution.

<Absorption Capacity Without Load (CRC)>:

An amount of 0.20 g of water-absorbent resin or particulate water-absorbent resin composition was weighed out precisely to a level of 0.0001 g and then uniformly placed and sealed into a bag made of nonwoven fabric (85 mm×60 mm).

A container of 1 L was charged with 1 L of 0.90 mass % aqueous sodium chloride solution, in which one evaluation sample per one container was then immersed for 1 hour. Incidentally, because the present invention is an invention made by directing attention to effects of ion transfer, more than one sample per one container must not be immersed.

After 1 hour, the bag was pulled up and then drained of water by centrifugal force (250 G) (as disclosed in edana ABSORBENCY II 441.1-99) with a centrifugal separator (produced by Kokusan Co., Ltd., centrifugal separator: model H-122) for 3 minutes, and then the mass W1 (g) of the bag was measured. In addition, the same procedure as the above was carried out without the water-absorbent resin or particulate water-absorbent resin composition, and the resultant mass W0 (g) was measured. Then, the absorption capacity (g/g) without load was calculated from these W1 and W0 in accordance with the following equation:

Absorption capacity (g/g) without load=[(W1 (g)−W0 (g))/mass (g) of water-absorbent resin or particulate water-absorbent resin composition]−1

<Specific-particle-diameter absorption capacity under load (AUL)>:

The specific-particle-diameter absorption capacity under load is an absorption capacity under load which is measured with particles (which pass through a JIS standard sieve of 600 μm, but do not pass through a JIS standard sieve of 300 μm) selected in order to eliminate the influence of the particle diameters on the water absorption rate.

A stainless metal gauze, which was a screen of 100 meshes (mesh opening size: 150 μm), was attached by fusion to a bottom of a plastic supporting cylinder having an inner diameter of 25.4 mm. Then, under conditions of a room temperature (20 to 25° C.) and a humidity of 50 RH %, onto the above metal gauze, there was uniformly spread 0.16 g of particulate water-absorbent resin composition, and further thereon, there were mounted a piston and a load in sequence, wherein the piston had an outer diameter of only a little smaller than 25.4 mm and made no gap with the supporting cylinder, but was not hindered from moving up and down, and wherein the piston and the load were adjusted so that a load of 0.01 psi (0.069 kPa), 0.29 psi (2.00 kPa), or 0.57 psi (3.93 kPa) could uniformly be applied to the particulate water-absorbent resin composition. Then, the mass Wa (g) of the resultant one set of measurement apparatus was measured.

A glass filter plate having a diameter of 90 mm (produced by Sogo Rikagaku Glass Seisakusho Co., Ltd., pore diameter: 100 to 120 μm) was mounted inside a Petri dish having a diameter of 150 mm, and then a 0.90 mass % aqueous sodium chloride solution (20 to 25° C.) was added up to the same level as the top surface of the glass filter plate, on which a filter paper having a diameter of 37 mm (Whatman, type: GF/A, cat No.1820 037) was then mounted so that its entire surface would be wetted, and further, an excess of liquid was removed.

The one set of measurement apparatus was mounted on the above wet filter paper, thereby getting the liquid absorbed under the load for predetermined periods. These absorption periods were defined as periods of 1 hour, 2 hours, 4 hours, 8 hours, and 20 hours from the start of the measurement. Specifically, 1 hour later, the one set of measurement apparatus was removed by being lifted to measure its mass Wb (g). This measurement of the mass must be carried out as quickly as possible and so as not to give any vibration. In addition, the load must not be removed during the measurement. Thereafter, the measurement apparatus was mounted on the aforementioned wet filter paper again, thereby getting the liquid absorbed in preparation for the next measurement of which the absorption periods were 2 hours, and further, 4 hours, 8 hours, and 20 hours. Incidentally, from beginning to end of the measurement, the liquid surface of the 0.90 mass % aqueous sodium chloride solution must be adjusted to the same level as the top surface of the glass filter plate.

Then, the specific-particle-diameter absorption capacity under load in each period ware calculated from the Wa and Wb in accordance with the following equation.

Specific-particle-diameter absorption capacity (g/g) under load=(Wb (g)−Wa (g))/mass (0.16 (g)) of particulate water-absorbent resin composition Incidentally, in the present invention, for convenience, the specific-particle-diameter absorption capacity under load when the load is "p" may be referred to as AUL (p), and the specific-particle-diameter absorption capacity under load when the absorption period is "q" may be referred to as AUL (q), and the specific-particle-diameter absorption capacity under load when the load is "p" and the absorption period is "q" may be referred to as AUL (p, q).

<Specific-particle-diameter Absorption Index>:

The specific-particle-diameter absorption index in the absorption period of "q" was defined by the following equation.

Specific-particle-diameter absorption index $(q)$=AUL (0.01 psi (0.069 kPa), $q$)+AUL (0.29 psi (2.00 kPa), $q$)

<Specific-particle-diameter Absorption Index Increment>:

The specific-particle-diameter absorption indexes in the absorption periods of 1 hour, 2 hours, 4 hours, 8 hours, and 20 hours were determined, and the difference between the determined values in 20 hours or 4 hours and in 1 hour was taken as the absorption index increment.

For example, the specific-particle-diameter absorption index increment in 20 hours is calculated as follows.

Specific-particle-diameter absorption index increment in 20 hours=specific-particle-diameter absorption index (20 hours)−specific-particle-diameter absorption index (1 hour)

<Mass-average particle diameter (D50) and logarithmic standard deviation (σζ)>:

The water-absorbent resin or particulate water-absorbent resin composition was classified with JIS standard sieves having mesh opening sizes of such as 850 μm, 710 μm, 600 μm, 500 μm, 425 μm, 300 μm, 212 μm, 150 μm, and 45 μm. Then, the percentages R of the residues on these sieves were plotted on a logarithmic probability paper. Therefrom, a particle diameter corresponding to R=50 mass % was read as the mass-average particle diameter (D50). In addition, the logarithmic standard deviation (σζ) is calculated in accordance with the following equation. The smaller σζ value shows the narrower particle diameter distribution.

$$\sigma\zeta = 0.5 \times ln(X2/X1)$$

(wherein: X1 is a particle diameter when R=84.1%, and X2 is a particle diameter when R=15.9%)

As to the classification method for measuring the mass-average particle diameter (D50) and the logarithmic standard deviation (σζ), 10.0 g of water-absorbent resin or particulate water-absorbent resin composition was placed onto JIS standard sieves (having mesh opening sizes of 850 μm, 600 μm, 300 μm, 150 μm, and 45 μm) (THE IIDA TESTING SIEVE: diameter=8 cm) under conditions of a room temperature (20 to 25° C.) and a humidity of 50 RH % and then classified with a shaking classifier (IIDA SIEVE SHAKER, TYPE: ES-65 type, SER. No. 0501) for 5 minutes.

<Extractable Component Content>:

Into a plastic receptacle of 250 ml in capacity having a lid, 184.3 g of 0.90 mass % aqueous sodium chloride solution (physiological saline solution) was weighed out. Then, 1.00 g of water-absorbent resin or particulate water-absorbent resin composition was added to this aqueous solution, and they were stirred for 16 hours, whereby extractable components were extracted from the resin. This extract liquid was filtrated with a filter paper (produced by ADVANTEC Toyo Co., Ltd., trade name: (JIS P 3801, No.2), thickness: 0.26 mm, diameter of captured particles: 5 μm), and then 50.0 g of the resultant filtrate was weighed out and used as the solution to be measured.

To begin with, only the 0.90 mass % aqueous sodium chloride solution (physiological saline solution) was firstly titrated with an aqueous 0.1N NaOH solution until the pH reached 10, and then the resultant solution was titrated with an aqueous 0.1N HCl solution until the pH reached 2.7, thus obtaining blank titration amounts ([bNaOH] ml and [bHCl] ml).

The same titration procedure was applied also to the solution to be measured, thus obtaining titration amounts ([NaOH] ml and [HCl] ml).

For example, if the water-absorbent resin or water-absorbent resin particles or particulate water-absorbent resin composition comprises acrylic acid and its sodium salt in already known amounts, then the extractable component content of the water-absorbent resin was calculated from the mass-average molecular weight of the monomers and the titration amounts (as obtained from the above procedures) in accordance with the following calculation equation. In the case of unknown amounts, the mass-average molecular weight of the monomers was calculated from the neutralization degree as determined by the titration.

Extractable component content (mass %)=0.1×(mass-average molecular weight)×184.3×100×([HCl]−[bHCl])/1000/1.0/50.0

Neutralization degree (mol %)=[1−([NaOH]−[bNaOH])/([HCl]−[bHCl])]×100

<Absorption Capacity under Load (AAP)>:

A stainless metal gauze, which was a screen of 400 meshes (mesh opening size: 38 μm), was attached by fusion to a bottom of a plastic supporting cylinder having an inner diameter of 60 mm. Then, under conditions of a room temperature (20 to 25° C.) and a humidity of 50 RH %, onto the above metal gauze, there was uniformly spread 0.90 g of particulate water-absorbent resin composition, and further thereon, there were mounted a piston and a load in sequence, wherein the piston had an outer diameter of only a little smaller than 60 mm and made no gap with the supporting cylinder, but was not hindered from moving up and down, and wherein the piston and the load were adjusted so that a load of 0.06 psi (0.41 kPa), 0.3 psi (2.06 kPa), or 0.7 psi (4.83 kPa) could uniformly be applied to the particulate water-absorbent resin composition. Then, the mass Wa (g) of the resultant one set of measurement apparatus was measured.

A glass filter plate having a diameter of 90 mm (produced by Sogo Rikagaku Glass Seisakusho Co., Ltd., pore diameter: 100 to 120 μm) was mounted inside a Petri dish having a diameter of 150 mm, and then a 0.90 mass % aqueous sodium chloride solution (20 to 25° C.) was added up to the same level as the top surface of the glass filter plate, on which a filter paper having a diameter of 90 mm (produced by ADVANTEC Toyo Co., Ltd., trade name: (JIS P 3801, No.2), thickness: 0.26 mm, diameter of captured particles: 5 μm) was then mounted so that its entire surface would be wetted, and further, an excess of liquid was removed.

The one set of measurement apparatus was mounted on the above wet filter paper, thereby getting the liquid absorbed under the load for predetermined periods. These absorption periods were defined as periods of 1 hour, 2 hours, 4 hours, 8 hours, and 20 hours from the start of the measurement. Specifically, 1 hour later, the one set of measurement apparatus was removed by being lifted to measure its mass Wb (g). This measurement of the mass must be carried out as quickly as possible and so as not to give any vibration. In addition, the load must not be removed during the measurement. Thereafter, the measurement apparatus was mounted on the aforementioned wet filter paper again, thereby getting the liquid absorbed in preparation for the next measurement of which the absorption periods were 2 hours, and further, 4 hours, 8 hours, and 20 hours. Incidentally, from beginning to end of the measurement, the liquid surface of the 0.90 mass % aqueous sodium chloride solution must be adjusted to the same level as the top surface of the glass filter plate.

Then, the absorption capacity under load in each period ware calculated from the Wa and Wb in accordance with the following equation.

Absorption capacity (g/g) under load=($Wb$ (g)−$Wa$ (g))/mass (0.9 (g)) of particulate water-absorbent resin composition Incidentally, in the present invention, for convenience, the absorption capacity under load when the load is "p" may be referred to as AAP (p), and the absorption capacity under load when the absorption period is "q" may be referred to as AAP (q), and the absorption capacity under load when the load is "p" and the absorption period is "q" may be referred to as AAP (p, q).

<Absorption Index>:

The absorption index in the absorption period of "q" was defined by the following equation.

Absorption index ($q$)=$AAP$ (0.06 psi (0.41 kPa), $q$)+$AAP$ (0.3 psi (2.06 kPa), $q$)

<Absorption Index Increment>:

The absorption indexes in the absorption periods of 1 hour, 2 hours, 4 hours, 8 hours, and 20 hours were determined, and the difference between the determined values in 20 hours or 4 hours and in 1 hour was taken as the absorption index increment.

For example, the absorption index increment in 20 hours is calculated as follows.

Absorption index increment in 20 hours=absorption index (20 hours)−absorption index (1 hour)

<Production of water-absorbent article>:

The water-absorbent article for evaluating its performances was produced by the following method.

First of all, 50 mass parts of each water-absorbent resin composition (having been obtained from the below-mentioned Examples and Comparative Examples) and 50 mass parts of wood-pulverized pulp were mixed together by a mixer in a dry manner. Next, the resultant mixture was pneumatically molded on a wire screen (having been formed into 400 meshes (mesh opening size: 38 μm)) with a batch type pneumatic molding apparatus and thereby shaped into a web of a size of 120 mm×400 mm. Furthermore, this web was pressed by a pressure of 2 kg/cm² (196.14 kPa) for 60 seconds, thus obtaining an absorbent structure having a basis mass of about 500 g/m². Subsequently, a back sheet made of liquid-impermeable polypropylene (liquid-impermeable sheet) (having what are called leg gathers), the above absorbent structure, and a top sheet made of liquid-permeable polypropylene (liquid-permeable sheet) were stuck on each other in that order with a double-coated tape, and then the resultant stuck material was provided with two so-called tape fasteners, thus obtaining a water-absorbent article (disposable diaper).

<Evaluation of Performances of Water-absorbent Article>:

The above water-absorbent article was put on a horizontal experimental stand in such a manner that the top sheet would be the upside, and then four corners of the water-absorbent article were fixed with a pressure sensitive adhesive tape in a state smoothed out so as to be wrinkle-free. Subsequently, thereon there was put a metal gauze (140 mm×400 mm) of 20 meshes (mesh opening size: 850 μm), and further thereon, there was put an acrylic plate (140 mm×400 mm) (in its central portion, there was set a cylinder of 70 mm in diameter and 50 mm in height) so that a liquid could be injected from a central portion. Incidentally, the mass of the acrylic plate as used was 1.5 kg. Subsequently, a weight of 4.25 kg was put on the acrylic plate and on each of opposite sides of the cylinder (total number of the weights: 2). The total of the masses of the acrylic plate and of the weights is 10 kg, so the load applied to the absorbent structure is 2.06 kPa. In this state, 75 ml of 0.90 mass % aqueous sodium chloride solution (physiological saline solution) was injected from the cylinder at a stroke to measure the time passing until the liquid went out of the cylinder. This time was defined as the liquid intake time. The water-absorbent article was left intact for 1 hour, and then the same operation was repeated to carry out the liquid injection 4 times to measure the first-time to fourth-time liquid intake times. Then, 1 hour later than the fourth-time liquid injection, the weights, acrylic plate, and metal gauze were quickly removed. Subsequently, a 30-ply paper towel (its mass was known, and its size was 140 mm×400 mm), a flat acrylic plate, and two weights (10 kg each) were mounted on the water-absorbent article. Then, 1 minute later, the weights were removed, and then the mass of the paper towel was measured to measure the wet-back amount from the change in mass of the paper towel.

The shorter the first-time to fourth-time liquid intake times are, the more excellent the absorption performances of the water-absorbent article are judged. In addition, the smaller the wet-back amount is, the more excellent the absorption performances are judged.

[Synthetic Example 1]

Synthesis of Water-absorbent Resin Particles (L-1)

A reaction liquid was prepared by putting 2,000 g of acrylic acid, 17.1 g of methylenebisacrylamide, and 7,724 g of water into a polyethylene-made beaker of 10 L and then dissolving them uniformly. Next, dissolved oxygen was removed from this reaction liquid under an atmosphere of nitrogen gas for 30 minutes. Subsequently, 60.5 g of 10 mass % aqueous V-50 (2,2'-azobis(2-amidinopropane) dihydrochloride) solution, 66.6 g of 3 mass % aqueous hydrogen peroxide solution, and 99.9 g of 0.5 mass % aqueous L-ascorbic acid solution were added thereto under stirred conditions. As a result, polymerization started after about 10 minutes. Then, polymerization was completed by leaving the reaction container alone at room temperature for 12 hours. Then, the resultant crosslinked hydrogel polymer was taken out and then pulverized with a meat chopper (produced by Iizuka Kogyo Co., Ltd., type: VR-400K, die diameter: 9.5 mm). The crosslinked hydrogel polymer having been divided into small pieces was spread onto a metal gauze of 50 meshes (mesh opening size: 300 μm) and then hot-air-dried at 150° C. for 1 hour. The resultant dried product was pulverized with a roll mill and then classified and regulated, thus obtaining water-absorbent resin particles (L-1) of an irregular pulverized shape.

As to the resultant water-absorbent resin particles (L-1), the absorption capacity without load (CRC) was 4.0 g/g, and the extractable component content was 2.9%.

The particle diameter distribution of the resultant water-absorbent resin particles (L-1) was as follows. Particles having particle diameters of smaller than 850 μm but not smaller than 600 μm: 19.4 mass %, particles having particle diameters of smaller than 600 μm but not smaller than 300 μm: 61.7 mass %, particles having particle diameters of smaller than 300 μm but not smaller than 150 μm: 16.8 mass %, particles having particle diameters of smaller than 150 μm but not smaller than 45 μm: 1.9 mass %, and particles having particle diameters of smaller than 45 μm: 0.2 mass %. In addition, mass-average particle diameter (D50)=426 μm, and logarithmic standard deviation ($\sigma\zeta$)=0.382.

Referential Example 1

Referential Example 1 investigated how the absorption behavior changed due to neutralization of an unneutralized water-absorbent resin. Incidentally, the measurement of the absorption capacity in Referential Example 1 adopted the following method different from the above measurement method of the absorption capacity without load (CRC).

An amount of 0.20 g of the water-absorbent resin particles (L-1) (having been obtained from Synthetic Example 1) was weighed out precisely to a level of 0.0001 g and then uniformly placed and sealed into a bag made of nonwoven fabric (85 mm×60 mm). Such samples were prepared to the number of 10.

A plastic-made container of 1,000 mL in capacity having a lid was charged with 1,000 mL of 0.90 mass % aqueous sodium chloride solution. Such containers were prepared to the number of 10. Added into these containers were sodium hydroxide needed for neutralizing 0%, 10%, 20%, 30%, 40%, 50%, 60%, 70%, 80%, and 90% respectively of the carboxyl groups of the resin components of the charged water-absorbent resin. After the addition of the sodium hydroxide, each of the aforementioned bags was immersed. After having been left intact for 20 hours, each bag was pulled up and then drained of water by centrifugal force (250 G) (as disclosed in edana ABSORBENCY II 441.1-99) with a centrifugal separator (produced by Kokusan Co., Ltd., centrifugal separator: model H-122) for 3 minutes, and then the mass W1 (g) of the bag was measured. In addition, the same procedure as the above was carried out without the water-absorbent resin, and the resultant mass W0 (g) was measured. Then, the absorption capacity (g/g) without load was calculated from these W1 and W0 in accordance with the following equation:

Absorption capacity (g/g) without load=[(W1 (g)−W0 (g))/{mass (g) of water-absorbent resin+ amount (g) of added NaOH×23/40}]−1

Shown in FIG. 1 are the results of Referential Example 1. It can be understood from FIG. 1 that: the relations between the neutralization degree and the absorption capacity are not proportional relations, but draw an upward convex type curve, and its inflection point is at a neutralization degree of 50%.

Synthetic Example 2

Synthesis of Water-absorbent Resin Particles (H-1)

In a reactor as prepared by lidding a jacketed stainless twin-arm kneader of 10 liters in capacity having two sigma-type blades, there was prepared a reaction liquid by dissolving 9.36 g (0.08 mol %) of polyethylene glycol diacrylate (molar-number-average degree of addition polymerization of ethylene oxide: 8) into 5,438 g of aqueous solution of sodium acrylate having a neutralization degree of 71.3 mol % (monomer concentration: 39 mass %). Next, dissolved oxygen was removed from this reaction liquid under an atmosphere of nitrogen gas for 30 minutes. Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out while the forming gel was pulverized. The polymerization initiation temperature was 20° C., and the highest temperature was 95° C. Then, the resultant crosslinked hydrogel polymer was taken out after 30 minutes from the start of the polymerization.

The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 180° C. for 50 minutes. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.4 g of 1,4-butanediol, 0.6 g of propylene glycol, and 2.7 g of pure water, and then the resultant mixture was heat-treated at 212° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (H-1).

As to the water-absorbent resin particles (H-1), the absorption capacity without load (CRC) was 27.7 g/g, and the extractable component content was 9.8%.

The particle diameter distribution of the water-absorbent resin particles (H-1) was as follows. Particles having particle diameters of smaller than 850 μm but not smaller than 600 μm: 18.8 mass %, particles having particle diameters of smaller than 600 μm but not smaller than 300 μm: 62.2 mass %, particles having particle diameters of smaller than 300 μm but not smaller than 150 μm: 17.9 mass %, particles having particle diameters of smaller than 150 μm but not smaller than 45 μm: 1.1 mass %, and particles having particle diameters of smaller than 45 μm: 0 mass %. In addition, mass-average particle diameter (D50)=423 μm, and logarithmic standard deviation ($\sigma\zeta$)=0.378.

Synthetic Example 3

Synthesis of Water-absorbent Resin Particles (L-2)

A reaction liquid was prepared by putting 2,000 g of acrylic acid, 4.275 g of methylenebisacrylamide, and 7,724 g of water into a polyethylene-made beaker of 10 L and then dissolving them uniformly. Next, dissolved oxygen was removed from this reaction liquid under an atmosphere of nitrogen gas for 30 minutes. Subsequently, 60.5 g of 10 mass % aqueous V-50 (2,2'-azobis(2-amidinopropane) dihydrochloride) solution, 66.6 g of 3 mass % aqueous hydrogen peroxide solution, and 99.9 g of 0.5 mass % aqueous L-ascorbic acid solution were added thereto under stirred conditions. As a result, polymerization started after about 10 minutes. Then, polymerization was completed by leaving the reaction container alone at room temperature for 12 hours. Then, the resultant crosslinked hydrogel polymer was taken out and then pulverized with a meat chopper (produced by Iizuka Kogyo Co., Ltd., type: VR-400K, die diameter: 9.5 mm). The crosslinked hydrogel polymer having been divided into small pieces was spread onto a metal gauze of 50 meshes (mesh opening size: 300 μm) and then hot-air-dried at 150° C. for 1 hour. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.1 g of ethylene glycol diglycidyl ether, 0.5 g of propylene glycol, 2 g of pure water, and 1 g of isopropanol, and then the resultant mixture was heat-treated at 150° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (L-2).

As to the water-absorbent resin particles (L-2), the absorption capacity without load (CRC) was 5.8 g/g, and the extractable component content was 7.2%.

The particle diameter distribution of the water-absorbent resin particles (L-2) was as follows. Particles having particle diameters of smaller than 850 μm but not smaller than 600 μm: 21.0 mass %, particles having particle diameters of smaller than 600 μm but not smaller than 300 μm: 62.1 mass %, particles having particle diameters of smaller than 300 μm but not smaller than 150 μm: 15.4 mass %, particles having particle diameters of smaller than 150 μm but not smaller than 45 μm: 1.5 mass %, and particles having particle diameters of smaller than 45 μm: 0 mass %. In addition, mass-average particle diameter (D50) =437 μm, and logarithmic standard deviation (σζ)=0.359.

Example 1

The water-absorbent resin particles (H-1) (having been obtained from Synthetic Example 2) and the water-absorbent resin particles (L-2) (having been obtained from Synthetic Example 3) were dry-blended in the mixing ratios (mass ratios) of 8:2, 7:3, 6:4, and 5:5, thus obtaining particulate water-absorbent resin compositions (1-1), (1-2), (1-3), and (1-4).

As to the resultant particulate water-absorbent resin compositions (1-1), (1-2), (1-3), and (1-4), the particle diameter distributions were the same as the weight-average values of the particle diameter distributions of the water-absorbent resin particles (H-1) and (L-2) having been used, and the mass-average particle diameters (D50) were in the range of 426 to 430 μm, and the logarithmic standard deviations (σζ) were in the range of 0.368 to 0.374.

The particle diameters of the resultant particulate water-absorbent resin compositions were regulated to particle diameters of smaller than 600 μm but not smaller than 300 μm. Shown in Table 1 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 1

Shown in Table 1 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-1) (having been obtained from Synthetic Example 2) alone of which the particle diameters had been regulated to particle diameters of smaller than 600 μm but not smaller than 300 μm.

Comparative Example 2

Shown in Table 1 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (L-2) (having been obtained from Synthetic Example 3) alone of which the particle diameters had been regulated to particle diameters of smaller than 600 μm but not smaller than 300 μm.

TABLE 1

| Sample | Mixing ratio | CRC | Measurement item | AUL and absorption index* | | | Specific-particle-diameter absorption index increment in 20 hr |
|---|---|---|---|---|---|---|---|
| | | | | 1 hr | 4 hr | 20 hr | |
| (1-1) | (H-1)/(L-2) = 8/2 | 26.9 | AUL0.01 psi | 39.1 | 41.8 | 42.0 | 4.9 |
| | | | AUL0.29 psi | 28.3 | 29.4 | 30.3 | |
| | | | AUL0.57 psi | 24.7 | 25.4 | 26.3 | |
| | | | Absorption index* | 67.4 | 71.2 | 72.3 | |
| (1-2) | (H-1)/(L-2) = 7/3 | 26.1 | AUL0.01 psi | 38.6 | 42.3 | 43.8 | 7.3 |
| | | | AUL0.29 psi | 27.5 | 29.2 | 29.6 | |
| | | | AUL0.57 psi | 23.7 | 24.2 | 24.6 | |
| | | | Absorption index* | 66.1 | 71.5 | 73.4 | |
| (1-3) | (H-1)/(L-2) = 6/4 | 24.8 | AUL0.01 psi | 34.8 | 40.2 | 41.0 | 8.5 |
| | | | AUL0.29 psi | 25.0 | 26.8 | 27.3 | |
| | | | AUL0.57 psi | 21.6 | 22.7 | 23.5 | |
| | | | Absorption index* | 59.8 | 67.0 | 68.3 | |

TABLE 1-continued

| Sample | Mixing ratio | CRC | Measurement item | AUL and absorption index* 1 hr | 4 hr | 20 hr | Specific-particle-diameter absorption index increment in 20 hr |
|---|---|---|---|---|---|---|---|
| (1-4) | (H-1)/(L-2) = 5/5 | 23.5 | AUL0.01 psi | 33.4 | 39.0 | 39.9 | 9.0 |
|  |  |  | AUL0.29 psi | 23.2 | 25.0 | 25.7 |  |
|  |  |  | AUL0.57 psi | 19.6 | 21.1 | 21.2 |  |
|  |  |  | Absorption index* | 56.6 | 64.0 | 65.6 |  |
| (H-1) | (H-1) alone | 27.7 | AUL0.01 psi | 37.1 | 37.5 | 37.0 | −0.1 |
|  |  |  | AUL0.29 psi | 30.2 | 30.4 | 30.2 |  |
|  |  |  | AUL0.57 psi | 26.8 | 27.2 | 27.4 |  |
|  |  |  | Absorption index* | 67.3 | 67.9 | 67.2 |  |
| (L-2) | (L-2) alone | 5.8 | AUL0.01 psi | 9.5 | 9.8 | 9.7 | 0.1 |
|  |  |  | AUL0.29 psi | 8.1 | 8.0 | 8.0 |  |
|  |  |  | AUL0.57 psi | 6.6 | 7.1 | 7.9 |  |
|  |  |  | Absorption index* | 17.6 | 17.8 | 17.7 |  |

*Specific-particle-diameter absorption index

Synthetic Example 4

Synthesis of Water-absorbent Resin Particles (H-2)

In a reactor as prepared by lidding a jacketed stainless twin-arm kneader of 10 liters in capacity having two sigma-type blades, there was prepared a reaction liquid by dissolving 7.02 g (0.06 mol %) of polyethylene glycol diacrylate (molar-number-average degree of addition polymerization of ethylene oxide: 8) into 5,500 g of aqueous solution of sodium acrylate having a neutralization degree of 71.3 mol % (monomer concentration: 38 mass %). Next, dissolved oxygen was removed from this reaction liquid under an atmosphere of nitrogen gas for 30 minutes. Subsequently, 24.6 g of 10 mass % aqueous sodium persulfate solution and 10 g of 0.1 mass % aqueous L-ascorbic acid solution were added thereto under stirred conditions. As a result, polymerization started after about 1 minute. Then, the polymerization was carried out while the forming gel was pulverized. The polymerization initiation temperature was 25° C., and the highest temperature was 95° C. Then, the resultant crosslinked hydrogel polymer was taken out after 40 minutes from the start of the polymerization.

The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 150° C. for 90 minutes. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.4 g of 1,4-butanediol, 0.6 g of propylene glycol, and 2.7 g of pure water, and then the resultant mixture was heat-treated at 210° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (H-2).

As to the water-absorbent resin particles (H-2), the absorption capacity without load (CRC) was 31.5 g/g, and the extractable component content was 12.5%.

The particle diameter distribution of the water-absorbent resin particles (H-2) was as follows. Particles having particle diameters of smaller than 850 μm but not smaller than 600 μm: 19.4 mass %, particles having particle diameters of smaller than 600 μm but not smaller than 300 μm: 61.7 mass %, particles having particle diameters of smaller than 300 μm but not smaller than 150 μm: 16.8 mass %, particles having particle diameters of smaller than 150 μm but not smaller than 45 μm: 1.9 mass %, and particles having particle diameters of smaller than 45 μm: 0.2 mass %. In addition, mass-average particle diameter (D50)=426 μm, and logarithmic standard deviation (σζ)=0.382.

Example 2

The water-absorbent resin particles (H-2) (having been obtained from Synthetic Example 4) and the water-absorbent resin particles (L-2) (having been obtained from Synthetic Example 3) were dry-blended in the mixing ratios (mass ratios) of 8:2 and 6:4, thus obtaining particulate water-absorbent resin compositions (2-1) and (2-2).

As to the resultant particulate water-absorbent resin compositions (2-1) and (2-2), the particle diameter distributions were the same as the weight-average values of the particle diameter distributions of the water-absorbent resin particles (H-2) and (L-2) having been used, and the mass-average particle diameters (D50) were in the range of 428 to 430 μm, and the logarithmic standard deviations (σζ) were in the range of 0.373 to 0.377.

The particle diameters of the resultant particulate water-absorbent resin compositions were regulated to particle diameters of smaller than 600 μm but not smaller than 300 μm. Shown in Table 2 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 3

Shown in Table 2 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-2) (having been obtained from Synthetic Example 4) alone of which the particle diameters had been regulated to particle diameters of smaller than 600 μm but not smaller than 300 μm.

opening size of 850 μm, thus obtaining surface-crosslink-treated water-absorbent resin particles (H-3).

As to the water-absorbent resin particles (H-3), the absorption capacity without load (CRC) was 36 g/g, and the extractable component content was 17%.

TABLE 2

| Sample | Mixing ratio | CRC | Measurement item | AUL and absorption index* | | | Specific-particle-diameter absorption index increment in 20 hr |
|---|---|---|---|---|---|---|---|
| | | | | 1 hr | 4 hr | 20 hr | |
| (2-1) | (H-2)/(L-2) = 8/2 | 29.7 | AUL0.01 psi | 41.4 | 44.8 | 45.5 | 5.3 |
| | | | AUL0.29 psi | 29.4 | 30.5 | 30.6 | |
| | | | AUL0.57 psi | 25.1 | 25.4 | 26.0 | |
| | | | Absorption index* | 70.8 | 75.3 | 76.1 | |
| (2-2) | (H-2)/(L-2) = 6/4 | 27.5 | AUL0.01 psi | 36.8 | 41.8 | 43.5 | 8.8 |
| | | | AUL0.29 psi | 25.8 | 27.5 | 27.9 | |
| | | | AUL0.57 psi | 22.0 | 22.8 | 23.5 | |
| | | | Absorption index* | 62.6 | 69.3 | 71.4 | |
| (H-2) | (H-2) alone | 31.5 | AUL0.01 psi | 43.9 | 44.1 | 44.2 | 0.7 |
| | | | AUL0.29 psi | 31.5 | 31.7 | 31.9 | |
| | | | AUL0.57 psi | 26.9 | 27.5 | 27.2 | |
| | | | Absorption index* | 75.4 | 75.8 | 76.1 | |

*Specific-particle-diameter absorption index

Synthetic Example 5

Synthesis of Water-absorbent Resin Particles (H-3)

In a reactor as prepared by lidding a jacketed stainless twin-arm kneader of 10 liters in capacity having two sigma-type blades, there was prepared a reaction liquid by dissolving 3.4 g (0.03 mol %) of polyethylene glycol diacrylate (molar-number-average degree of addition polymerization of ethylene oxide: 8) into 5,500 g of aqueous solution of sodium acrylate having a neutralization degree of 75 mol % (monomer concentration: 38 mass %). Next, dissolved oxygen was removed from this reaction liquid under an atmosphere of nitrogen gas for 30 minutes. Subsequently, 24.6 g of 10 mass % aqueous sodium persulfate solution and 10 g of 0.1 mass % aqueous L-ascorbic acid solution were added thereto under stirred conditions. As a result, polymerization started after about 1 minute. Then, the polymerization was carried out while the forming gel was pulverized. The polymerization initiation temperature was 25° C., and the highest temperature was 95° C. Then, the resultant crosslinked hydrogel polymer was taken out after 40 minutes from the start of the polymerization.

The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 150° C. for 90 minutes. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.03 g of ethylene glycol diglycidyl ether, 0.3 g of 1,4-butanediol, 0.5 g of propylene glycol, and 3 g of pure water, and then the resultant mixture was heat-treated at 2.10° C. for 55 minutes. Furthermore, the resultant particles were disintegrated to such a degree that they could pass through a JIS standard sieve having a mesh opening size of 850 μm, thus obtaining surface-crosslink-treated water-absorbent resin particles (H-3).

The particle diameter distribution of the water-absorbent resin particles (H-3) was as follows. Particles having particle diameters of smaller than 850 μm but not smaller than 600 μm: 20.5 mass %, particles having particle diameters of smaller than 600 μm but not smaller than 300 μm: 61.9 mass %, particles having particle diameters of smaller than 300 μm but not smaller than 150 μm: 15.5 mass %, particles having particle diameters of smaller than 150 μm but not smaller than 45 μm: 1.8 mass %, and particles having particle diameters of smaller than 45 μm: 0.3 mass %. In addition, mass-average particle diameter (D50)=433 μm, and logarithmic standard deviation (σζ)=0.368.

Example 3

The water-absorbent resin particles (H-3) (having been obtained from Synthetic Example 5) and the water-absorbent resin particles (L-2) (having been obtained from Synthetic Example 3) were dry-blended in the mixing ratios (mass ratios) of 8:2 and 6:4, thus obtaining particulate water-absorbent resin compositions (3-1) and (3-2).

As to the resultant particulate water-absorbent resin compositions (3-1) and (3-2), the particle diameter distributions were the same as the weight-average values of the particle diameter distributions of the water-absorbent resin particles (H-3) and (L-2) having been used, and the mass-average particle diameters (D50) were in the range of 434 to 435 μm, and the logarithmic standard deviations (σζ) were in the range of 0.364 to 0.366.

The particle diameters of the resultant particulate water-absorbent resin compositions were regulated to particle diameters of smaller than 600 μm but not smaller than 300 μm. Shown in Table 3 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 4

Shown in Table 3 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-3) (having been obtained from Synthetic Example 5) alone of which the particle diameters had been regulated to particle diameters of smaller than 600 μm but not smaller than 300 μm.

TABLE 3

| Sample | Mixing ratio | CRC | Measurement item | AUL and absorption index* | | | Specific-particle-diameter absorption index increment in 20 hr |
|---|---|---|---|---|---|---|---|
| | | | | 1 hr | 4 hr | 20 hr | |
| (3-1) | (H-3)/(L-2) = 8/2 | 35.4 | AUL0.01 psi | 45.8 | 48.6 | 49.3 | 3.5 |
| | | | AUL0.29 psi | 29.8 | 30.2 | 29.8 | |
| | | | AUL0.57 psi | 24.5 | 25.4 | 25.5 | |
| | | | Absorption index* | 75.6 | 78.8 | 79.1 | |
| (3-2) | (H-3)/(L-2) = 6/4 | 31.4 | AUL0.01 psi | 40.0 | 44.3 | 45.6 | 6.7 |
| | | | AUL0.29 psi | 26.7 | 27.8 | 27.8 | |
| | | | AUL0.57 psi | 21.8 | 21.8 | 22.7 | |
| | | | Absorption index* | 66.7 | 72.1 | 73.4 | |
| (H-3) | (H-3) alone | 36.0 | AUL0.01 psi | 49.0 | 49.8 | 47.5 | −2.7 |
| | | | AUL0.29 psi | 34.0 | 34.0 | 32.8 | |
| | | | AUL0.57 psi | 28.3 | 28.1 | 27.8 | |
| | | | Absorption index* | 83.0 | 83.8 | 80.3 | |

*Specific-particle-diameter absorption index

Synthetic Example 6

Synthesis of Water-absorbent Resin Particles (H-4)

In a reactor as prepared by lidding a jacketed stainless twin-arm kneader of 10 liters in capacity having two sigma-type blades, there was prepared a reaction liquid by dissolving 3.4 g (0.03 mol %) of polyethylene glycol diacrylate (molar-number-average degree of addition polymerization of ethylene oxide: 8) into 5,500 g of aqueous solution of sodium acrylate having a neutralization degree of 75 mol % (monomer concentration: 33 mass %). Next, dissolved oxygen was removed from this reaction liquid under an atmosphere of nitrogen gas for 30 minutes. Subsequently, 24.6 g of 10 mass % aqueous sodium persulfate solution and 10 g of 0.1 mass % aqueous L-ascorbic acid solution were added thereto under stirred conditions. As a result, polymerization started after about 1 minute. Then, the polymerization was carried out while the forming gel was pulverized. The polymerization initiation temperature was 20° C., and the highest temperature was 95° C. Then, the resultant crosslinked hydrogel polymer was taken out after 40 minutes from the start of the polymerization.

The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 150° C. for 90 minutes. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.03 g of ethylene glycol diglycidyl ether, 0.3 g of 1,4-butanediol, 0.5 g of propylene glycol, and 3 g of pure water, and then the resultant mixture was heat-treated at 200° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (H-4).

As to the water-absorbent resin particles (H-4), the absorption capacity without load (CRC) was 45 g/g, and the extractable component content was 30%.

The particle diameter distribution of the water-absorbent resin particles (H4) was as follows. Particles having particle diameters of smaller than 850 μm but not smaller than 600 μm: 20.3 mass %, particles having particle diameters of smaller than 600 μm but not smaller than 300 μm: 62.8 mass %, particles having particle diameters of smaller than 300 μm but not smaller than 150 μm: 15.8 mass %, particles having particle diameters of smaller than 150 μm but not smaller than 45 μm: 1.1 mass %, and particles having particle diameters of smaller than 45 μm: 0 mass %. In addition, mass-average particle diameter (D50)=435 μm, and logarithmic standard deviation ($\sigma\zeta$)=0.357.

Example 4

The water-absorbent resin particles (H-4) (having been obtained from Synthetic Example 6) and the water-absorbent resin particles (L-2) (having been obtained from Synthetic Example 3) were dry-blended in the mixing ratios (mass ratios) of 8:2 and 6:4, thus obtaining particulate water-absorbent resin compositions (4-1) and (4-2).

As to the resultant particulate water-absorbent resin compositions (4-1) and (4-2), the particle diameter distributions were the same as the weight-average values of the particle diameter distributions of the water-absorbent resin particles (H-4) and (L-2) having been used, and the mass-average particle diameters (D50) were in the range of 435 to 436 μm, and the logarithmic standard deviations ($\sigma\zeta$) were 0.358.

The particle diameters of the resultant particulate water-absorbent resin compositions were regulated to particle diameters of smaller than 600 μm but not smaller than 300 μm. Shown in Table 4 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 5

Shown in Table 4 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-4) (having been obtained from Synthetic Example 6) alone of which the particle diameters had been regulated to particle diameters of smaller than 600 μm but not smaller than 300 μm.

hot-air-dried at 150° C. for 1 hour. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.1 g of ethylene glycol diglycidyl ether, 0.5 g of propylene glycol, 2 g of pure water, and 1 g of isopropanol, and then the resultant mixture was heat-treated at 150° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (L-3).

As to the water-absorbent resin particles (L-3), the absorption capacity without load (CRC) was 7.3 g/g, and the extractable component content was 5.3%.

The particle diameter distribution of the water-absorbent resin particles (L-3) was as follows. Particles having particle diameters of smaller than 850 μm but not smaller than 600 μm: 18.3 mass %, particles having particle diameters of

TABLE 4

| Sample | Mixing ratio | CRC | Measurement item | AUL and absorption index* | | | Specific-particle-diameter absorption index increment in 20 hr |
|---|---|---|---|---|---|---|---|
| | | | | 1 hr | 4 hr | 20 hr | |
| (4-1) | (H-4)/(L-2) = 8/2 | 42.0 | AUL0.01 psi | 47.0 | 51.5 | 51.7 | 4.6 |
| | | | AUL0.29 psi | 30.1 | 30.3 | 30.0 | |
| | | | AUL0.57 psi | 19.5 | 19.8 | 22.5 | |
| | | | Absorption index* | 77.1 | 81.8 | 81.7 | |
| (4-2) | (H-4)/(L-2) = 6/4 | 35.6 | AUL0.01 psi | 43.7 | 48.1 | 48.4 | 5.1 |
| | | | AUL0.29 psi | 25.8 | 26.0 | 26.2 | |
| | | | AUL0.57 psi | 16.9 | 17.9 | 21.2 | |
| | | | Absorption index* | 69.5 | 74.1 | 74.6 | |
| (H-4) | (H-4) alone | 45.1 | AUL0.01 psi | 53.0 | 53.5 | 52.1 | −2.0 |
| | | | AUL0.29 psi | 32.2 | 31.8 | 31.1 | |
| | | | AUL0.57 psi | 20.7 | 20.6 | 23.1 | |
| | | | Absorption index* | 85.2 | 85.3 | 83.2 | |

*Specific-particle-diameter absorption index

Synthetic Example 7

Synthesis of Water-absorbent Resin Particles (L-3)

A reaction liquid was prepared by putting 5,200 g of aqueous solution of acrylic acid of 10 mol % in neutralization degree (monomer concentration: 20 mass %) and 2.16 g of methylenebisacrylamide into a polyethylene-made beaker of 10 L and then dissolving them uniformly. Next, dissolved oxygen was removed from this reaction liquid under an atmosphere of nitrogen gas for 30 minutes. Subsequently, 15 g of 20 mass % aqueous V-50 (2,2'-azobis(2-amidinopropane) dihydrochloride) solution, 10 g of 10 mass % aqueous hydrogen peroxide solution, and 5 g of 5 mass % aqueous L-ascorbic acid solution were added thereto under stirred conditions. As a result, polymerization started after about 5 minutes. Then, polymerization was completed by leaving the reaction container alone at room temperature for 12 hours. Then, the resultant crosslinked hydrogel polymer was taken out and then pulverized with a meat chopper (produced by Iizuka Kogyo Co., Ltd., type: VR-400K, die diameter: 9.5 mm). The crosslinked hydrogel polymer having been divided into small pieces was spread onto a metal gauze of 50 meshes (mesh opening size: 300 μm) and then smaller than 600 μm but not smaller than 300 μm: 62.8 mass %, particles having particle diameters of smaller than 300 μm but not smaller than 150 μm: 16.5 mass %, particles having particle diameters of smaller than 150 μm but not smaller than 45 μm: 2.2 mass %, and particles having particle diameters of smaller than 45 μm: 0.2 mass %. In addition, mass-average particle diameter (D50)=422 μm, and logarithmic standard deviation (σζ)=0.384.

Synthetic Example 8

Synthesis of Water-absorbent Resin Particles (L-4)

A reaction liquid was prepared by putting 5,200 g of aqueous solution of acrylic acid of 20 mol % in neutralization degree (monomer concentration: 20 mass %) and 8.6 g of methylenebisacrylamide into a polyethylene-made beaker of 10 L and then dissolving them uniformly. Next, dissolved oxygen was removed from this reaction liquid under an atmosphere of nitrogen gas for 30 minutes. Subsequently, 15 g of 20 mass % aqueous V-50 (2,2'-azobis(2-amidinopropane) dihydrochloride) solution, 10 g of 10 mass % aqueous hydrogen peroxide solution, and 5 g of 5 mass % aqueous L-ascorbic acid solution were added thereto under stirred conditions. As a result, polymerization started after about 5 minutes. Then, polymerization was completed by leaving the reaction container alone at room temperature for 12 hours. Then, the resultant crosslinked hydrogel polymer was taken out and then pulverized with a meat chopper (produced by Iizuka Kogyo Co., Ltd., type: VR-400K, die diameter: 9.5 mm). The crosslinked hydrogel polymer having been divided into small pieces was spread onto a metal gauze of 50 meshes (mesh opening size: 300 μm) and then hot-air-dried at 150° C. for 1 hour. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.1 g of ethylene glycol diglycidyl ether, 0.5 g of propylene glycol, 2 g of pure water, and 1 g of isopropanol, and then the resultant mixture was heat-treated at 150° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (L-4).

As to the water-absorbent resin particles (L-4), the absorption capacity without load (CRC) was 18 g/g, and the extractable component content was 3%.

The particle diameter distribution of the water-absorbent resin particles (L-4) was as follows. Particles having particle diameters of smaller than 850 μm but not smaller than 600 μm: 20.0 mass %, particles having particle diameters of smaller than 600 μm but not smaller than 300 μm: 60.7 mass %, particles having particle diameters of smaller than 300 μm but not smaller than 150 μm: 16.2 mass %, particles having particle diameters of smaller than 150 μm but not smaller than 45 μm: 2.9 mass %, and particles having particle diameters of smaller than 45 μm: 0.2 mass %. In addition, mass-average particle diameter (D50)=426 μm, and logarithmic standard deviation (σζ)=0.393.

Example 5

The water-absorbent resin particles (H-1) (having been obtained from Synthetic Example 2) were dry-blended with either the water-absorbent resin particles (L-3) (having been obtained from Synthetic Example 7) or the water-absorbent resin particles (L-4) (having been obtained from Synthetic Example 8) in the mixing ratio (mass ratio) of 6:4, thus obtaining particulate water-absorbent resin compositions (5-1) and (5-2).

As to the resultant particulate water-absorbent resin compositions (5-1) and (5-2), the particle diameter distributions were the same as the weight-average value of the particle diameter distributions of the water-absorbent resin particles (H-1) and either (L-3) or (L-4) having been used, and the mass-average particle diameters (D50) were in the range of 423 to 425 μm, and the logarithmic standard deviations (σζ) were in the range of 0.380 to 0.383.

The particle diameters of the resultant particulate water-absorbent resin compositions were regulated to particle diameters of smaller than 600 μm but not smaller than 300 μm. Shown in Table 5 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 6

Shown in Table 5 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (L-3) (having been obtained from Synthetic Example 7) alone of which the particle diameters had been regulated to particle diameters of smaller than 600 μm but not smaller than 300 μm.

Comparative Example 7

Shown in Table 5 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (L-4) (having been obtained from Synthetic Example 8) alone of which the particle diameters had been regulated to particle diameters of smaller than 600 μm but not smaller than 300 μm.

TABLE 5

| Sample | Mixing ratio | CRC | Measurement item | AUL and absorption index* | | | Specific-particle-diameter absorption index increment in 20 hr |
|---|---|---|---|---|---|---|---|
| | | | | 1 hr | 4 hr | 20 hr | |
| (5-1) | (H-1)/(L-3) = 6/4 | 23.4 | AUL0.01 psi | 33.7 | 36.8 | 38.0 | 6.1 |
| | | | AUL0.29 psi | 25.8 | 27.2 | 27.6 | |
| | | | AUL0.57 psi | 22.0 | 22.6 | 23.6 | |
| | | | Absorption index* | 59.5 | 64.0 | 65.6 | |
| (5-2) | (H-1)/(L-4) = 6/4 | 26.0 | AUL0.01 psi | 38.6 | 40.5 | 41.1 | 3.9 |
| | | | AUL0.29 psi | 28.4 | 29.0 | 29.8 | |
| | | | AUL0.57 psi | 25.0 | 25.7 | 26.4 | |
| | | | Absorption index* | 67.0 | 69.5 | 70.9 | |
| (L-3) | (L-3) alone | 7.3 | AUL0.01 psi | 14.2 | 14.3 | 14.1 | 0.9 |
| | | | AUL0.29 psi | 10.0 | 10.4 | 11.0 | |
| | | | AUL0.57 psi | 9.2 | 10.1 | 10.2 | |
| | | | Absorption index* | 24.2 | 24.7 | 25.1 | |
| (L-4) | (L-4) alone | 18.0 | AUL0.01 psi | 27.6 | 28.1 | 27.8 | 1.0 |
| | | | AUL0.29 psi | 18.5 | 19.2 | 19.3 | |

TABLE 5-continued

| Sample | Mixing ratio | CRC | Measurement item | AUL and absorption index* 1 hr | 4 hr | 20 hr | Specific-particle-diameter absorption index increment in 20 hr |
|---|---|---|---|---|---|---|---|
| | | | AUL0.57 psi | 15.0 | 16.0 | 16.3 | |
| | | | Absorption index* | 46.1 | 47.3 | 47.1 | |

*Specific-particle-diameter absorption index

Synthetic Example 9

Synthesis of Water-absorbent Resin Particles (H-5)

In a reactor as prepared by lidding a jacketed stainless twin-arm kneader of 10 liters in capacity having two sigma-type blades, there was prepared a reaction liquid by dissolving 7.3 g (0.05 mol %) of polyethylene glycol diacrylate (molar-number-average degree of addition polymerization of ethylene oxide: 8) into 6,570 g of aqueous solution of sodium acrylate having a neutralization degree of 60 mol % (monomer concentration: 39 mass %). Next, dissolved oxygen was removed from this reaction liquid under an atmosphere of nitrogen gas for 30 minutes. Subsequently, 24.6 g of 10 mass % aqueous sodium persulfate solution and 10 g of 0.1 mass % aqueous L-ascorbic acid solution were added thereto under stirred conditions. As a result, polymerization started after about 1 minute. Then, the polymerization was carried out while the forming gel was pulverized. The polymerization initiation temperature was 20° C., and the highest temperature was 95° C. Then, the resultant crosslinked hydrogel polymer was taken out after 40 minutes from the start of the polymerization.

The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 180° C. for 50 minutes. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.5 g of glycerol, 2 g of pure water, and 0.5 g of isopropanol, and then the resultant mixture was heat-treated at 212° C. for 30 minutes. Furthermore, the resultant particles were disintegrated to such a degree that they could pass through a JIS standard sieve having a mesh opening size of 850 μm, thus obtaining surface-crosslink-treated water-absorbent resin particles (H-5).

As to the water-absorbent resin particles (H-5), the absorption capacity without load (CRC) was 23 g/g, and the extractable component content was 13%.

The particle diameter distribution of the water-absorbent resin particles (H-5) was as follows. Particles having particle diameters of smaller than 850 μm but not smaller than 600 μm: 17.7 mass %, particles having particle diameters of smaller than 600 μm but not smaller than 300 μm: 63.4 mass %, particles having particle diameters of smaller than 300 μm but not smaller than 150 μm: 15.5 mass %, particles having particle diameters of smaller than 150 μm but not smaller than 45 μm: 3.2 mass %, and particles having particle diameters of smaller than 45 μm: 0.2 mass %. In addition, mass-average particle diameter (D50)=421 μm, and logarithmic standard deviation (σζ)=0.390.

Example 6

The water-absorbent resin particles (H-5) (having been obtained from Synthetic Example 9) were dry-blended with each of the water-absorbent resin particles (L-2) (having been obtained from Synthetic Example 3), the water-absorbent resin particles (L-3) (having been obtained from Synthetic Example 7), and the water-absorbent resin particles (L-4) (having been obtained from Synthetic Example 8) in the mixing ratio (mass ratio) of 6:4, thus obtaining particulate water-absorbent resin compositions (6-1), (6-2), and (6-3).

As to the resultant particulate water-absorbent resin compositions (6-1), (6-2), and (6-3), the particle diameter distributions were the same as the weight-average value of the particle diameter distributions of the water-absorbent resin particles (H-5) and each of (L-2), (L-3), and (L-4) having been used, and the mass-average particle diameters (D50) were in the range of 421 to 427 μm, and the logarithmic standard deviations (σ70) were in the range of 0.376 to 0.391.

The particle diameters of the resultant particulate water-absorbent resin compositions were regulated to particle diameters of smaller than 600 μm but not smaller than 300 μm. Shown in Table 6 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 8

Shown in Table 6 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-5) (having been obtained from Synthetic Example 9) alone of which the particle diameters had been regulated to particle diameters of smaller than 600 μm but not smaller than 300 μm.

TABLE 6

| Sample | Mixing ratio | CRC | Measurement item | AUL and absorption index* 1 hr | 4 hr | 20 hr | Specific-particle-diameter absorption index increment in 20 hr |
|---|---|---|---|---|---|---|---|
| (6-1) | (H-5)/(L-2) = 6/4 | 22.0 | AUL0.01 psi | 31.0 | 35.4 | 36.2 | 7.7 |
|  |  |  | AUL0.29 psi | 20.4 | 21.5 | 22.9 |  |
|  |  |  | AUL0.57 psi | 16.6 | 17.0 | 18.8 |  |
|  |  |  | Absorption index* | 51.4 | 56.9 | 59.1 |  |
| (6-2) | (H-5)/(L-3) = 6/4 | 19.8 | AUL0.01 psi | 31.2 | 33.1 | 34.2 | 4.9 |
|  |  |  | AUL0.29 psi | 22.2 | 22.9 | 24.1 |  |
|  |  |  | AUL0.57 psi | 18.6 | 19.2 | 20.3 |  |
|  |  |  | Absorption index* | 53.4 | 56.0 | 58.3 |  |
| (6-3) | (H-5)/(L-4) = 6/4 | 23.1 | AUL0.01 psi | 35.4 | 36.9 | 37.4 | 3.8 |
|  |  |  | AUL0.29 psi | 24.6 | 25.4 | 26.4 |  |
|  |  |  | AUL0.57 psi | 20.3 | 21.2 | 22.0 |  |
|  |  |  | Absorption index* | 60.0 | 62.3 | 63.8 |  |
| (H-5) | (H-5) alone | 22.9 | AUL0.01 psi | 36.5 | 36.0 | 35.9 | −0.2 |
|  |  |  | AUL0.29 psi | 25.4 | 25.3 | 25.8 |  |
|  |  |  | AUL0.57 psi | 21.8 | 22.3 | 22.6 |  |
|  |  |  | Absorption index* | 61.9 | 61.3 | 61.7 |  |

*Specific-particle-diameter absorption index

Synthetic Example 10

Synthesis of Water-absorbent Resin Particles (H-6)

In a reactor as prepared by lidding a jacketed stainless twin-arm kneader of 10 liters in capacity having two sigma-type blades, there was prepared a reaction liquid by dissolving 15 g (0.1 mol %) of polyethylene glycol diacrylate (molar-number-average degree of addition polymerization of ethylene oxide: 8) into 6,570 g of aqueous solution of sodium acrylate having a neutralization degree of 50 mol % (monomer concentration: 39 mass %). Next, dissolved oxygen was removed from this reaction liquid under an atmosphere of nitrogen gas for 30 minutes.

Subsequently, 29.34 g of 10 mass % aqueous sodium persulfate solution and 24.45 g of 0.1 mass % aqueous L-ascorbic acid solution were added thereto under stirred conditions. As a result, polymerization started after about 1 minute. Then, the polymerization was carried out while the forming gel was pulverized. The polymerization initiation temperature was 20° C., and the highest temperature was 95° C. Then, the resultant crosslinked hydrogel polymer was taken out after 30 minutes from the start of the polymerization.

The crosslinked hydrogel polymer as obtained was what had been divided into small pieces having diameters of not larger than about 5 mm. This crosslinked hydrogel polymer having been divided into small pieces was spread onto a metal gauze of 50 meshes (mesh opening size: 300 μm) and then hot-air-dried at 180° C. for 50 minutes. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.32 g of 1,4-butanediol, 0.5 g of propylene glycol, 2.73 g of pure water, and 0.45 g of isopropanol, and then the resultant mixture was heat-treated at 205° C. for 10 minutes. Furthermore, the resultant particles were disintegrated to such a degree that they could pass through a JIS standard sieve having a mesh opening size of 850 μm, thus obtaining surface-crosslink-treated water-absorbent resin particles (H-6).

As to the water-absorbent resin particles (H-6), the absorption capacity without load (CRC) was 23.6 g/g, and the extractable component content was 7%.

The particle diameter distribution of the water-absorbent resin particles (H-6) was as follows. Particles having particle diameters of smaller than 850 μm but not smaller than 600 μm: 22.7 mass %, particles having particle diameters of smaller than 600 μm but not smaller than 300 μm: 58.6 mass %, particles having particle diameters of smaller than 300 μm but not smaller than 150 μm: 17.7 mass %, particles having particle diameters of smaller than 150 μm but not smaller than 45 μm: 1.0 mass %, and particles having particle diameters of smaller than 45 μm: 0 mass %. In addition, mass-average particle diameter (D50)=437 μm, and logarithmic standard deviation (σζ)=0.373.

Example 7

The water-absorbent resin particles (H-6) (having been obtained from Synthetic Example 10) were dry-blended with each of the water-absorbent resin particles (L-2) (having been obtained from Synthetic Example 3), the water-absorbent resin particles (L-3) (having been obtained from Synthetic Example 7), and the water-absorbent resin particles (L-4) (having been obtained from Synthetic Example 8) in the mixing ratio (mass ratio) of 6:4, thus obtaining particulate water-absorbent resin compositions (7-1), (7-2), and (7-3).

As to the resultant particulate water-absorbent resin compositions (7-1), (7-2), and (7-3), the particle diameter distributions were the same as the weight-average value of the particle diameter distributions of the water-absorbent resin particles (H-6) and each of (L-2), (L-3), and (L-4) having been used, and the mass-average particle diameters (D50) were in the range of 431 to 437 μm, and the logarithmic standard deviations (σζ) were in the range of 0.368 to 0.381.

The particle diameters of the resultant particulate water-absorbent resin compositions were regulated to particle diameters of smaller than 600 μm but not smaller than 300 μm. Shown in Table 7 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

Comparative Example 9

Shown in Table 7 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-6) (having been obtained from Synthetic Example 10) alone of which the particle diameters had been regulated to particle diameters of smaller than 600 μm but not smaller than 300 μm.

TABLE 7

| Sample | Mixing ratio | CRC | Measurement item | AUL and absorption index* | | | Specific-particle-diameter absorption index |
|---|---|---|---|---|---|---|---|
| | | | | 1 hr | 4 hr | 20 hr | Increment in 20 hr |
| (7-1) | (H-6)/(L-2) = 6/4 | 21.3 | AUL0.01 psi | 29.0 | 32.5 | 33.5 | 5.1 |
| | | | AUL0.29 psi | 20.5 | 20.7 | 21.1 | |
| | | | AUL0.57 psi | 16.4 | 16.7 | 17.5 | |
| | | | Absorption index* | 48.7 | 53.2 | 54.6 | |
| (7-2) | (H-6)/(L-3) = 6/4 | 18.8 | AUL0.01 psi | 29.9 | 31.4 | 31.9 | 4.0 |
| | | | AUL0.29 psi | 21.2 | 22.5 | 23.2 | |
| | | | AUL0.57 psi | 18.4 | 19.1 | 20.2 | |
| | | | Absorption index* | 51.1 | 53.9 | 55.1 | |
| (7-3) | (H-6)/(L-4) = 6/4 | 20.4 | AUL0.01 psi | 34.1 | 35.4 | 36.2 | 3.3 |
| | | | AUL0.29 psi | 24.3 | 24.6 | 25.5 | |
| | | | AUL0.57 psi | 20.1 | 20.5 | 21.4 | |
| | | | Absorption index* | 58.4 | 60.0 | 61.7 | |
| (H-6) | (H-6) alone | 23.6 | AUL0.01 psi | 35.6 | 35.6 | 35.6 | 0.3 |
| | | | AUL0.29 psi | 25.4 | 25.5 | 25.7 | |
| | | | AUL0.57 psi | 21.4 | 21.6 | 22.5 | |
| | | | Absorption index* | 61.0 | 61.1 | 61.3 | |

*Specific-particle-diameter absorption index

Synthetic Example 11

Synthesis of Water-absorbent Resin Particles (H-7)

A reaction liquid was prepared by putting 6,400 g of aqueous solution of acrylic acid of 90 mol % in neutralization degree (monomer concentration: 20 mass %) and 8.63 g of methylenebisacrylamide into a polyethylene-made beaker of 10 L and then dissolving them uniformly. Next, dissolved oxygen was removed from this reaction liquid under an atmosphere of nitrogen gas for 30 minutes. Subsequently, 15.3 g of 20 mass % aqueous V-50 (2,2'-azobis(2-amidinopropane) dihydrochloride) solution, 10 g of 10 mass % aqueous hydrogen peroxide solution, and 5 g of 5 mass % aqueous L-ascorbic acid solution were added thereto under stirred conditions. As a result, polymerization started after about 5 minutes. Then, polymerization was completed by leaving the reaction container alone at room temperature for 12 hours. Then, the resultant crosslinked hydrogel polymer was taken out and then pulverized with a meat chopper (produced by Iizuka Kogyo Co., Ltd., type: VR-400K, die diameter: 9.5 mm). The crosslinked hydrogel polymer having been divided into small pieces was spread onto a metal gauze of 50 meshes (mesh opening size: 300 μm) and then hot-air-dried at 150° C. for 1 hour. The resultant dried product was pulverized with a roll mill and then classified and regulated, thus obtaining water-absorbent resin particles of an irregular pulverized shape.

An amount of 100 g of the water-absorbent resin particles as obtained were mixed with a surface-treating agent comprising a mixed liquid of 0.1 g of ethylene glycol diglycidyl ether, 0.5 g of propylene glycol, 2 g of pure water, and 1 g of isopropanol, and then the resultant mixture was heat-treated at 195° C. for 40 minutes. Furthermore, the resultant particles were disintegrated to such a degree that they could pass through a JIS standard sieve having a mesh opening size of 850 μm, thus obtaining surface-crosslink-treated water-absorbent resin particles (H-7).

As to the water-absorbent resin particles (H-7), the absorption capacity without load (CRC) was 37 g/g, and the extractable component content was 12.3%.

The particle diameter distribution of the water-absorbent resin particles (H-7) was as follows. Particles having particle diameters of smaller than 850 μm but not smaller than 600 μm: 24.0 mass %, particles having particle diameters of smaller than 600 μm but not smaller than 300 μm: 57.6 mass %, particles having particle diameters of smaller than 300 μm but not smaller than 1.50 μm: 16.8 mass %, particles having particle diameters of smaller than 150 μm but not smaller than 45 μm: 1.5 mass %, and particles having particle diameters of smaller than 45 μm: 0.1 mass %. In addition, mass-average particle diameter (D50)=442 μm, and logarithmic standard deviation (σζ)=0.374.

Example 8

The water-absorbent resin particles (H-7) (having been obtained from Synthetic Example 11) were dry-blended with the water-absorbent resin particles (L-2) (having been obtained from Synthetic Example 3) in the mixing ratio (mass ratio) of 6:4, thus obtaining a particulate water-absorbent resin composition (8-1).

As to the resultant particulate water-absorbent resin composition (8-1), the particle diameter distribution was the same as the weight-average value of the particle diameter distributions of the water-absorbent resin particles (H-7) and (L-2) having been used, and the mass-average particle diameter (D50) was 440 μm, and the logarithmic standard deviation (σζ) was 0.368.

The particle diameters of the resultant particulate water-absorbent resin composition were regulated to particle diameters of smaller than 600 μm but not smaller than 300 μm. Shown in Table 8 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours.

Comparative Example 10

Shown in Table 8 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the water-absorbent resin particles (H-7) (having been obtained from Synthetic Example 11) alone of which the particle diameters had been regulated to particle diameters of smaller than 600 μm but not smaller than 300 μm.

than 150 μm: 15.4 mass %, particles having particle diameters of smaller than 150 μm but not smaller than 45 μm: 1.5 mass %, and particles having particle diameters of smaller than 45 μm: 0 mass %. In addition, mass-average particle diameter (D50)=437 μm, and logarithmic standard deviation (σζ)=0.359.

(L-7): Particles having particle diameters of smaller than 600 μm but not smaller than 500 μm: 50 mass % and particles having particle diameters of smaller than 500 μm but not smaller than 300 μm: 50 mass %. In addition, mass-average particle diameter (D50)=500 μm.

Example 9

In Example 9, in order to measure a change of the absorption rate under a wide range of particle diameter conditions, the absorption capacity under load (AAP) and the absorption index were measured instead of the above-mentioned measurement of the absorption capacity under load and the absorption index within the specific particle

TABLE 8

| Sample | Mixing ratio | CRC | Measurement item | AUL and absorption index* | | | Specific-particle-diameter absorption index |
| --- | --- | --- | --- | --- | --- | --- | --- |
| | | | | 1 hr | 4 hr | 20 hr | Increment in 20 hr |
| (8-1) | (H-7)/(L-2) = 6/4 | 33.0 | AUL0.01 psi | 44.4 | 49.0 | 50.0 | 7.2 |
| | | | AUL0.29 psi | 24.9 | 25.8 | 26.5 | |
| | | | AUL0.57 psi | 11.3 | 14.7 | 19.9 | |
| | | | Absorption index* | 69.3 | 74.8 | 76.5 | |
| (H-7) | (H-7) alone | 37.0 | AUL0.01 psi | 51.7 | 51.3 | 50.4 | 0.3 |
| | | | AUL0.29 psi | 22.0 | 24.0 | 23.6 | |
| | | | AUL0.57 psi | 9.5 | 12.9 | 19.3 | |
| | | | Absorption index* | 73.7 | 75.3 | 74.0 | |

*Specific-particle-diameter absorption index

Synthetic Example 12

Syntheses of Water-absorbent Resin Particles (L-5), (L-6), and (L-7)

The unneutralized water-absorbent resin particles (having been obtained from Synthetic Example 3) were regulated so as to have the following particle diameter distributions, thus obtaining particles (L-5), (L-6), and (L-7) having different particle diameters.

(L-5): Particles having particle diameters of smaller than 850 μm but not smaller than 600 μm: 5 mass %, particles having particle diameters of smaller than 600 μm but not smaller than 300 μm: 64.9 mass %, particles having particle diameters of smaller than 300 μm but not smaller than 150 μm: 27 mass %, particles having particle diameters of smaller than 150 μm but not smaller than 45 μm: 2.5 mass %, and particles having particle diameters of smaller than 45 μm: 0.7 mass %. In addition, mass-average particle diameter (D50)=354 μm.

(L-6): Used with the particle diameters left as it had been obtained from Synthetic Example 3. Specifically, they were as follows. Particles having particle diameters of smaller than 850 μm but not smaller than 600 μm: 21.0 mass %, particles having particle diameters of smaller than 600 μm but not smaller than 300 μm: 62.1 mass %, particles having particle diameters of smaller than 300 μm but not smaller diameter range (specific-particle-diameter absorption capacity under load and specific-particle-diameter absorption index).

The water-absorbent resin particles (H-1) (having been obtained from Synthetic Example 2) were dry-blended with each of the water-absorbent resin particles (L-5), (L-6), and (L-7) (having been obtained from Synthetic Example 12) in the mixing ratio (mass ratio) of 6:4, and then water was added thereto in an amount of 2 mass % to mix them together under stirring, and then the resultant mixture was left intact for 1 hour and then passed through a sieve of 850 μm in mesh opening size, thus obtaining agglomerated particulate water-absorbent resin compositions (9-1), (9-2), and (9-3).

(9-1): Particles having particle diameters of smaller than 850 μm but not smaller than 600 μm: 15.2 mass %, particles having particle diameters of smaller than 600 μm but not smaller than 300 μm: 65.5 mass %, particles having particle diameters of smaller than 300 μm but not smaller than 150 μm: 19.2 mass %, particles having particle diameters of smaller than 150 μm but not smaller than 45 μm: 0.1 mass %, and particles having particle diameters of smaller than 45 μm: 0 mass %. In addition, mass-average particle diameter (D50)=412 μm, and logarithmic standard deviation (σζ)=0.362.

(9-2): Particles having particle diameters of smaller than 850 μm but not smaller than 600 μm: 21 mass %, particles having particle diameters of smaller than 600 µm but not smaller than 300 µm: 64.5 mass %, particles having particle diameters of smaller than 300 µm but not smaller than 150 µm: 14.3 mass %, particles having particle diameters of smaller than 150 µm but not smaller than 45 µm: 0.2 mass %, and particles having particle diameters of smaller than 45 µm: 0 mass %. In addition, mass-average particle diameter (D50)=445 µm, and logarithmic standard deviation (σζ) =0.336.

(9-3): Particles having particle diameters of smaller than 850 µm but not smaller than 600 µm: 13 mass %, particles having particle diameters of smaller than 600 µm but not smaller than 300 µm: 79.5 mass %, particles having particle diameters of smaller than 300 µm but not smaller than 150 µm: 7.4 mass %, particles having particle diameters of smaller than 150 µm but not smaller than 45 µm: 0.1 mass %, and particles having particle diameters of smaller than 45 µm: 0 mass %. In addition, mass-average particle diameter (D50)=443 µm, and logarithmic standard deviation (σζ) =0.27.

Shown in Table 9 are the CRC, AAP (0.06 psi (0.41 kPa)) in each absorption period, AAP (0.3 psi (2.06 kPa)) in each absorption period, AAP (0.7 psi (4.83 kPa)) in each absorption period, absorption indexes in each absorption period, and absorption index increments in 20 hours of the resultant particulate water-absorbent resin compositions.

Synthetic Example 13

Synthesis of Water-absorbent Resin Particles (H-8)

The water-absorbent resin particles (H-1) (having been obtained from Synthetic Example 2) were regulated so as to be particles of smaller than 300 µm but not smaller than 150 µm, thus obtaining water-absorbent resin particles (H-8) of mass-average particle diameter (D50)=225 µm.

Comparative Example 11

The water-absorbent resin particles (H-8) (having been obtained from Synthetic Example 13) and the water-absorbent resin particles (L-7) (having been obtained from Synthetic Example 12) were dry-blended in the mixing ratio (mass ratio) of 6:4, and then water was added thereto in an amount of 2 mass % to mix them together under stirring, and then the resultant mixture was left intact for 1 hour and then passed through a sieve of 850 µm in mesh opening size, thus obtaining an agglomerated particulate water-absorbent resin composition (c11-1).

(c11-1): Particles having particle diameters of smaller than 850 µm but not smaller than 600 µm: 2 mass %, particles having particle diameters of smaller than 600 µm but not smaller than 300 µm: 43.3 mass %, particles having particle diameters of smaller than 300 µm but not smaller than 150 µm: 54.7 mass %, particles having particle diameters of smaller than 150 µm but not smaller than 45 µm: 0 mass %, and particles having particle diameters of smaller than 45 µm: 0 mass %. In addition, mass-average particle diameter (D50)=300 µm, and logarithmic standard deviation (σζ)=0.158.

Shown in Table 9 are the CRC, AAP (0.06 psi (0.41 kPa)) in each absorption period, AAP (0.3 psi (2.06 kPa)) in each absorption period, AAP (0.7 psi (4.83 kPa)) in each absorption period, absorption index in each absorption period, and absorption index increment in 20 hours of the resultant particulate water-absorbent resin composition.

Comparative Example 12

Water-absorbent resin particles (H-9) and water-absorbent resin particles (L-8) were obtained by regulating the water-absorbent resin particles (H-3) (having been obtained from Synthetic Example 5) and the water-absorbent resin particles (L-3) (having been obtained from Synthetic Example 7) so that they would have the following particle diameters. Particles having particle diameters of smaller than 850 µm but not smaller than 600 µm: 2 mass %, particles having particle diameters of smaller than 600 µm but not smaller than 300 µm: 45.5 mass %, particles having particle diameters of smaller than 300 µm but not smaller than 150 µm: 47.5 mass %, particles having particle diameters of smaller than 150 µm but not smaller than 45 µm: 4.5 mass %, and particles having particle diameters of smaller than 45 µm: 0.5 mass %. In addition, mass-average particle diameter (D50)=292 µm.

The resultant water-absorbent resin particles (H-9) and water-absorbent resin particles (L-8) were dry-blended in the mixing ratio (mass ratio) of 6:4, and then water was added thereto in an amount of 2 mass % to mix them together under stirring, and then the resultant mixture was left intact for 1 hour and then passed through a sieve of 850 µm in mesh opening size, thus obtaining an agglomerated particulate water-absorbent resin composition (c12-1).

(c12-1): Particles having particle diameters of smaller than 850 µm but not smaller than 600 µm: 2 mass %, particles having particle diameters of smaller than 600 µm but not smaller than 300 µm: 46.7 mass %, particles having particle diameters of smaller than 300 µm but not smaller than 150 µm: 48.7 mass %, particles having particle diameters of smaller than 150 µm but not smaller than 45 µm: 2.6 mass %, and particles having particle diameters of smaller than 45 µm: 0 mass %. In addition, mass-average particle diameter (D50)=297 µm, and logarithmic standard deviation (σζ)=0.347.

Shown in Table 9 are the CRC, AAP (0.06 psi (0.41 kPa)) in each absorption period, AAP (0.3 psi (2.06 kPa)) in each absorption period, AAP (0.7 psi (4.83 kPa)) in each absorption period, absorption index in each absorption period, and absorption index increment in 20 hours of the resultant particulate water-absorbent resin composition.

Comparative Example 13

The water-absorbent resin particles (H-1) (having been obtained from Synthetic Example 2) were sieve-classified so as to be in the range of smaller than 850 µm but not smaller than 600 µm, thus obtaining water-absorbent resin particles (H-10).

Shown in Table 9 are the CRC, AAP (0.06 psi (0.41 kPa)) in each absorption period, AAP (0.3 psi (2.06 kPa)) in each absorption period, AAP (0.7 psi (4.83 kPa)) in each absorption period, absorption index in each absorption period, and absorption index increment in 20 hours of the resultant water-absorbent resin particles (H-10) alone.

Comparative Example 14

Shown in Table 9 are the CRC, AAP (0.06 psi (0.41 kPa)) in each absorption period, AAP (0.3 psi (2.06 kPa)) in each absorption period, AAP (0.7 psi (4.83 kPa)) in each absorption period, absorption index in each absorption period, and absorption index increment in 20 hours of the water-absorbent resin particles (L-7) (having been obtained from Synthetic Example 12) alone.

TABLE 9

| Sample | Mixing ratio | CRC | Measurement item | AAP and absorption index | | | Absorption index increment in 20 hr |
|---|---|---|---|---|---|---|---|
| | | | | 1 hr | 4 hr | 20 hr | |
| (9-1) | (H-1)/(L-5) = 6/4 | 27.1 | AAP0.06 psi | 30.7 | 32.6 | 33.9 | 5.4 |
| | | | AAP0.3 psi | 23.9 | 25.3 | 26.1 | |
| | | | AAP0.7 psi | 17.9 | 19.1 | 20.1 | |
| | | | Absorption index | 54.6 | 57.9 | 60.0 | |
| (9-2) | (H-1)/(L-6) = 6/4 | 26.4 | AAP0.06 psi | 29.4 | 32.1 | 33.8 | 7.6 |
| | | | AAP0.3 psi | 23.3 | 25.4 | 26.5 | |
| | | | AAP0.7 psi | 19.2 | 20.6 | 21.4 | |
| | | | Absorption index | 52.7 | 57.5 | 60.3 | |
| (9-3) | (H-1)/(L-7) = 6/4 | 25.8 | AAP0.06 psi | 29.3 | 32.7 | 34.4 | 8.8 |
| | | | AAP0.3 psi | 22.7 | 25.1 | 26.4 | |
| | | | AAP0.7 psi | 18.5 | 20.1 | 21.0 | |
| | | | Absorption index | 52.0 | 57.8 | 60.8 | |
| (c11-1) | (H-8)/(L-7) = 6/4 | 26.8 | AAP0.06 psi | 30.7 | 31.7 | 32.4 | 2.6 |
| | | | AAP0.3 psi | 24.1 | 24.5 | 25.0 | |
| | | | AAP0.7 psi | 18.8 | 19.2 | 20.0 | |
| | | | Absorption index | 54.8 | 56.2 | 57.4 | |
| (c12-1) | (H-9)/(L-8) = 6/4 | 28.5 | AAP0.06 psi | 33.9 | 35.3 | 35.8 | 2.4 |
| | | | AAP0.3 psi | 26.0 | 26.4 | 26.5 | |
| | | | AAP0.7 psi | 19.8 | 19.6 | 20.4 | |
| | | | Absorption index | 59.9 | 61.7 | 62.3 | |
| (H-10) | (H-10) alone | 28.0 | AAP0.06 psi | 38.2 | 38.8 | 38.2 | 0.5 |
| | | | AAP0.3 psi | 30.2 | 30.8 | 30.7 | |
| | | | AAP0.7 psi | 24.6 | 25.5 | 25.3 | |
| | | | Absorption index | 68.4 | 69.6 | 68.9 | |
| (L-7) | (L-7) alone | 4.6 | AAP0.06 psi | 9.6 | 10.1 | 9.7 | 0.4 |
| | | | AAP0.3 psi | 7.5 | 7.8 | 7.8 | |
| | | | AAP0.7 psi | 6.5 | 6.7 | 6.5 | |
| | | | Absorption index | 17.1 | 17.9 | 17.5 | |

Comparative Example 15

In order to demonstrate the water absorption behavior in cases where water-absorbent resins having high neutralization degrees were mixed together, particulate water-absorbent resin compositions were produced in the following combinations, thus obtaining the particulate water-absorbent resin compositions (c15-1) and (c15-2).

(c15-1): A particulate water-absorbent resin composition (mass-average particle diameter (D50)=428 μm, logarithmic standard deviation (σζ)=0.369) obtained by mixing the water-absorbent resin particles (H-1) (having been obtained from Synthetic Example 2) and the water-absorbent resin particles (H4) (having been obtained from Synthetic Example 6) in the mixing ratio (mass ratio) of 6:4.

(c15-2): A particulate water-absorbent resin composition (mass-average particle diameter (D50)=428 μm, logarithmic standard deviation (σζ)=0.377) obtained by mixing the water-absorbent resin particles (H-3) (having been obtained from Synthetic Example 5) and the water-absorbent resin particles (H-5) (having been obtained from Synthetic Example 9) in the mixing ratio (mass ratio) of 6:4.

The particle diameters of the resultant particulate water-absorbent resin compositions (c15-1) and (c15-2) were regulated to particle diameters of smaller than 600 μm but not smaller than 300 μm. Shown in Table 10 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption indexes in each absorption period, and specific-particle-diameter absorption index increments in 20 hours.

TABLE 10

| Sample | Mixing ratio | CRC | Measurement item | AUL and absorption index* | | | Specific-particle-diameter absorption index Increment in 20 hr |
|---|---|---|---|---|---|---|---|
| | | | | 1 hr | 4 hr | 20 hr | |
| (c15-1) | (H-1)/(H-4) = 6/4 | 33.9 | AUL0.01 psi | 46.9 | 47.6 | 46.2 | −0.8 |
| | | | AUL0.29 psi | 31.8 | 32.3 | 31.7 | |
| | | | AUL0.57 psi | 26.5 | 26.5 | 26.5 | |
| | | | Absorption index* | 78.7 | 79.9 | 77.9 | |

TABLE 10-continued

| Sample | Mixing ratio | CRC | Measurement item | AUL and absorption index* | | | Specific-particle-diameter absorption index |
| --- | --- | --- | --- | --- | --- | --- | --- |
| | | | | 1 hr | 4 hr | 20 hr | Increment in 20 hr |
| (c15-2) | (H-3)/(H-5) = 6/4 | 31.0 | AUL0.01 psi | 42.2 | 42.4 | 42.1 | −0.3 |
| | | | AUL0.29 psi | 29.0 | 28.9 | 28.8 | |
| | | | AUL0.57 psi | 23.3 | 23.1 | 23.5 | |
| | | | Absorption index* | 71.2 | 71.3 | 70.9 | |

*Specific-particle-diameter absorption index

Comparative Example 16

A particulate water-absorbent resin composition (c16-1), to which fine particles of poly(acrylic acid) had been added, was obtained by the same process as of Example 4 as described in JP-A-098170/2001 (Kokai).

Shown in Table 11 are the CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours of the resultant particulate water-absorbent resin composition (c16-1).

TABLE 11

| Sample | CRC | Measurement item | AUL and absorption index* | | | Specific-particle-diameter absorption index increment in 20 hr |
| --- | --- | --- | --- | --- | --- | --- |
| | | | 1 hr | 4 hr | 20 hr | |
| JP-A-098170/2001 (Kokai) Example 4 | 37 | AUL0.01 psi | 48.0 | 47.9 | 46.4 | 0 |
| | | AUL0.29 psi | 28.2 | 29.9 | 29.8 | |
| | | AUL0.57 psi | 16.3 | 20.1 | 23.1 | |
| | | Absorption index* | 76.2 | 77.8 | 76.2 | |

*Specific-particle-diameter absorption index

Example 10

In accordance with the aforementioned process, water-absorbent articles were produced from the particulate water-absorbent resin compositions (1-1) and (1-3) (having been obtained from Example 1) and the water-absorbent resin particles (H-1) (having been obtained from Synthetic Example 2) to evaluate the performances. The results are shown in Table 12.

TABLE 12

| Particulate water-absorbent resin composition or water-absorbent resin particles used | Particulate water-absorbent resin composition (1-1) | Particulate water-absorbent resin composition (1-3) | Water-absorbent resin particles (H-1) |
| --- | --- | --- | --- |
| First-time liquid intake time (seconds) | 10 | 8 | 10 |
| Second-time liquid intake time (seconds) | 20 | 18 | 25 |
| Third-time liquid intake time (seconds) | 23 | 20 | 30 |
| Fourth-time liquid intake time (seconds) | 25 | 22 | 31 |
| Wet-back amount (g) | 2.5 | 7.3 | 7.4 |

Example 11

A sodium carbonate powder (produced by Kanto Chemical Co., Inc.) was regulated so as to have the same particle diameters as of the water-absorbent resin particles (L-4) (having been obtained from Synthetic Example 8). Then, the water-absorbent resin particles (L-4) and the above-regulated sodium carbonate powder were mixed in the mixing ratio (mass ratio) of 8:2, thus obtaining a particulate water-absorbent resin composition (11-1).

As to the resultant particulate water-absorbent resin composition (11-1), the particle diameter distribution was almost equal to that of the water-absorbent resin particles (L-4) having been used, and the mass-average particle diameter (D50) was 425 μm, and the logarithmic standard deviation (σζ) was 0.390.

The particle diameters of the resultant particulate water-absorbent resin composition were regulated to particle diameters of smaller than 600 μm but not smaller than 300 μm. Shown in Table 13 are the resultant CRC, AUL (0.01 psi (0.069 kPa)) in each absorption period, AUL (0.29 psi (2.00 kPa)) in each absorption period, AUL (0.57 psi (3.93 kPa)) in each absorption period, specific-particle-diameter absorption index in each absorption period, and specific-particle-diameter absorption index increment in 20 hours.

TABLE 13

| Sample | Mixing ratio | CRC | Measurement item | AUL and absorption index* | | | Specific-particle-diameter absorption index |
|---|---|---|---|---|---|---|---|
| | | | | 1 hr | 4 hr | 20 hr | increment in 20 hr |
| (11-1) | (L-4)/sodium carbonate = 8/2 | 20.2 | AUL0.01 psi | 30.4 | 31.9 | 32.3 | 4.3 |
| | | | AUL0.29 psi | 20.1 | 21.8 | 22.5 | |
| | | | AUL0.57 psi | 15.8 | 17.5 | 19 | |
| | | | Absorption index* | 50.5 | 53.7 | 54.8 | |

*Specific-particle-diameter absorption index

INDUSTRIAL APPLICATION

Because the particulate water-absorbent resin composition according to the present invention has the excellent water absorption properties, this particulate water-absorbent resin composition can be used as water-absorbing and water-retaining agents for water-absorbent articles, namely, various purposes. For example, this composition can be used for such as: water-absorbing and water-retaining agents for absorbent articles (e.g. disposable diapers, sanitary napkins, incontinent pads, and medical pads); agricultural and horticultural water-retaining agents (e.g. substitutes for peat moss, soil-modifying-and-improving agents, water-retaining agents, and agents for duration of effects of agricultural chemicals); water-retaining agents for buildings (e.g. dew-condensation-preventing agents for interior wall materials, cement additives); release control agents; coldness-retaining agents; disposable portable body warmers; sludge-solidifying agents; freshness-retaining agents for foods; ion-exchange column materials; dehydrating agents for sludge or oil; desiccating agents; and humidity-adjusting materials. In addition, the particulate water-absorbent resin composition according to the present invention can be used particularly favorably for sanitary materials for absorption of excrement, urine, or blood, such as disposable diapers and sanitary napkins.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A particulate water-absorbent resin composition, which is a particulate water-absorbent resin composition comprising at least two kinds of carboxyl-group-containing water-absorbent resins having different neutralization degrees in an amount of not smaller than 80 mass %,
    with the composition being:
    in the range of 320 to 700 μm in mass-average particle diameter;
    not less than 20 g/g in absorption capacity under load (0.3 psi (2.06 kPa), 1 hour); and
    not less than 3 g/g in absorption index increment in 20 hours.

2. A particulate water-absorbent resin composition according to claim 1, which has not less than 20 g/g in specific-particle-diameter absorption capacity under load (0.29 psi (2.00 kPa), 1 hour); and not less than 3 g/g in specific-particle-diameter absorption index increment in 20 hours, wherein the content of particles having particle diameters in the range of 300 to 600 μm (but not including 600 μm) in the particulate water-absorbent resin composition is not lower than 50 mass %.

3. A particulate water-absorbent resin composition according to claim 1, wherein the specific-particle-diameter absorption index increment is not less than 6 g/g.

4. A particulate water-absorbent resin composition according to claim 2, wherein the absorption index increment is not less than 6 g/g.

5. A particulate water-absorbent resin composition according to claim 1, comprising a carboxyl-group-containing water-absorbent resin (A) of not less than 50% in neutralization degree of the carboxyl groups and a carboxyl-group-containing water-absorbent resin (B) of less than 50% in neutralization degree of the carboxyl groups in a mass ratio of (A):(B)=90:10 to 10:90, wherein there is a difference of not less than 30% between the neutralization degrees of the carboxyl-group-containing water-absorbent resins (A) and (B).

6. A particulate water-absorbent resin composition according to claim 5, wherein both of the carboxyl-group-containing water-absorbent resins (A) and (B) have a mass-average particle diameter of not smaller than 320 μm.

7. A particulate water-absorbent resin composition according to claim 5, wherein the carboxyl-group-containing water-absorbent resins (A) and (B) are both surface-treated ones.

8. A particulate water-absorbent resin composition according to claim 1, which is lower than 5 mass % in content of particles having particle diameters of smaller than 150 μm.

9. A particulate water-absorbent resin composition according to claim 1, which partly comprises agglomerated water-absorbent resin particles formed by agglomeration treatment.

10. A particulate water-absorbent resin composition according to claim 1, which is not more than 0.46 in logarithmic standard deviation σζ of particle diameter distribution.

11. A particulate water-absorbent resin composition according to claim 5, which is not less than 11 in neutralization degree-absorption capacity-mixing index.

12. A particulate water-absorbent resin composition according to claim 5, which is not less than 22 in neutralization degree-absorption capacity-mixing index.

13. A water-absorbent article, comprising the particulate water-absorbent resin composition as recited in claim 1.

14. A water-absorbent article, comprising the particulate water-absorbent resin composition as recited in claim 2.

15. A particulate water-absorbent resin composition according to claim 2, comprising a carboxyl-group-containing water-absorbent resin (A) of not less than 50% in neutralization degree of the carboxyl groups and a carboxyl-group-containing water-absorbent resin (B) of less than 50% in neutralization degree of the carboxyl groups in a mass ratio of (A):(B)=90:10 to 10:90, wherein there is a difference of not less than 30% between the neutralization degrees of the carboxyl-group-containing water-absorbent resins (A) and (B).

16. A particulate water-absorbent resin composition according to claim 1, wherein the carboxyl-group-containing water-absorbent resins are obtained by aqueous solution polymerizations.

17. A particulate water-absorbent resin composition according to claim 2, wherein the carboxyl-group-containing water-absorbent resins are obtained by aqueous solution polymerizations.

18. A particulate water-absorbent resin composition according to claim 5, wherein the carboxyl-group-containing water-absorbent resins are obtained by aqueous solution polymerizations.

19. A particulate water-absorbent resin composition according to claim 15, wherein the carboxyl-group-containing water-absorbent resins are obtained by aqueous solution polymerizations.

* * * * *